United States Patent
Goldman et al.

(10) Patent No.: US 7,496,173 B2
(45) Date of Patent: Feb. 24, 2009

(54) METHOD AND SYSTEM FOR OPTIMIZING DOSE DELIVERY OF RADIATION

(75) Inventors: Samuel Pedro Goldman, London (CA); Jeff Z. Chen, London (CA); Jerry J. Battista, London (CA)

(73) Assignee: University of Western Ontario, London, Ontario (CA)

( * ) Notice: Subject to any disclaimer, the term of this patent is extended or adjusted under 35 U.S.C. 154(b) by 204 days.

(21) Appl. No.: 10/581,885

(22) PCT Filed: Dec. 10, 2004

(86) PCT No.: PCT/CA2004/002108

§ 371 (c)(1),
(2), (4) Date: Jun. 6, 2006

(87) PCT Pub. No.: WO2005/057463

PCT Pub. Date: Jun. 23, 2005

(65) Prior Publication Data

US 2007/0127623 A1   Jun. 7, 2007

Related U.S. Application Data

(60) Provisional application No. 60/528,775, filed on Dec. 12, 2003, provisional application No. 60/566,433, filed on Apr. 30, 2004, provisional application No. 60/602,631, filed on Aug. 19, 2004.

(51) Int. Cl.
*A61N 5/10* (2006.01)
(52) U.S. Cl. ........................................ 378/65
(58) Field of Classification Search ............. 378/65
See application file for complete search history.

(56) References Cited

U.S. PATENT DOCUMENTS 6,038,283 A   3/2000   Carol et al.

(Continued)

FOREIGN PATENT DOCUMENTS

CA   2587587   6/2005

(Continued)

OTHER PUBLICATIONS

S Webb, "The physical basis of IMRT and inverse planning," The British Journal of Radiology, 76, 678-689, 2003.

(Continued)

*Primary Examiner*—Chih-Cheng G Kao
(74) *Attorney, Agent, or Firm*—Bereskin & Parr

(57) ABSTRACT

The invention relates to methods and systems for computationally efficient optimization of radiation dose delivery that involve determining an objective function to be used for mapping radiotherapy beams to a patient body volume having at least one target volume and at least one non-target volume. The objective function has a first term related to the at least one target volume and a second term related to the at least one non-target volume. The second term is zero only if the weights of beamlets mapped so as to pass through the non-target volume(s) are zero. The second term helps to avoid the occurrence of negative beam weights, thereby facilitating computationally efficient optimization using matrix inversion. An optimal set of weights of beamlets is determined using the objective function. Radiotherapy is delivered based on the determined optimal set of weights.

45 Claims, 12 Drawing Sheets

U.S. PATENT DOCUMENTS

| | | | |
|---|---|---|---|
| 6,152,599 | A | 11/2000 | Salter, Jr. |
| 6,546,073 | B1 | 4/2003 | Lee |
| 6,714,620 | B2 | 3/2004 | Caflisch et al. |
| 2002/0008915 | A1 | 1/2002 | Koster |
| 2002/0080915 | A1 | 6/2002 | Frolich |
| 2003/0212325 | A1 | 11/2003 | Cotrutz et al. |
| 2005/0111621 | A1 | 5/2005 | Riker et al. |
| 2007/0201614 | A1* | 8/2007 | Goldman et al. .............. 378/65 |

FOREIGN PATENT DOCUMENTS

| | | |
|---|---|---|
| WO | WO 03/099380 | 12/2003 |

OTHER PUBLICATIONS

S.P. Goldman, J.Z. Chen, and J.J. Battista, "Fast Inverse Dose Optimization (FIDO) for IMRT via Matrix Inversion with no Negative Intensities," XIVth International Conference on the Use of Computers in Radiation Therapy, pp. 112-115, May 11, 2004.

S.P. Goldman, J.Z. Chen and J.J. Battista, "Feasibility of fast inverse dose optimization algorithm for IMRT via matrix inversion without negative beamlet intensities," Med. Phys. 32(9), 3007-3016, Aug. 30, 2005.

Starkschall G, "A constrained least-squares optimization method for external beam radiation therapy treatment planning." Medical Physics Sep.-Oct. 1984, vol. 11, No. 5, Sep. 1984, pp. 659-665, ISBN: 0094-2405.

Censor Y,"Mathematical aspects of radiation therapy treatment planning: continuous inversion versus full discretization and optimization versus feasibility." Computational Radiology and Imaging: Therapy and Diagnostic, vol. 110, 1999, pp. 1-12.

Hilbig Matthias et al, "Design of an inverse planning system for radiotherapy using linear optimization Entwicklung eines inversen Bestrahlungsplanungssystems mit linearer Optimierung", Zeitschrift Fuer Medizinische Physik, Urban Fischer, Jena, DE, vol. 12, No. 2, 2002, pp. 89-96, ISBN: 0939-3889.

International Search Report dated Aug. 5, 2008 from related International Application No. PCT/CA2008/000834.

Spirou et al., "Smoothing intensity-modulated beam profiles to improve the efficiency of delivery", Medical Physics, vol. 28, Issue 10, Oct. 2001, pp. 2105-2112.

* cited by examiner

METHOD AND SYSTEM FOR OPTIMIZING DOSE DELIVERY OF RADIATION

FIELD OF THE INVENTION

The present invention relates to methods and systems for optimizing dose delivery of radiation. In particular, the present invention relates to efficient and effective methods of determining a minimum of an objective function for planning dose delivery of radiation.

BACKGROUND OF THE INVENTION

For cancer patients, radiation therapy is recognized as a valuable form of treatment. Radiation therapy involves the transmission of radiation energy to a tumor site within the patient.

Radiation therapy planning may be carried out according to a forward planning technique or an inverse planning technique. Forward planning involves delivering an initial planned radiation dose and then delivering subsequent doses by observation or inference of the efficacy of the preceding dose in a trial-and-error manner. The optimization of dose delivery by forward planning is therefore performed according to human observation and experience. Inverse planning instead seeks to calculate an optimized dose delivery and then work backwards to determine the appropriate radiation beam characteristics to deliver that optimized dose.

Inverse planning of radiation therapy for tumors may be performed for Tomotherapy or Intensity Modulated Radiation Therapy (IMRT) radiation delivery techniques. Both of these techniques involve transmission of radiation beams, usually collimated by a multi-leaf collimator (MLC), toward the tumor site from various angular orientations. For Tomotherapy, a helical arc is employed to irradiate the tumor slice by slice, while for IMRT multiple intensity-modulated conical beams are used to irradiate the tumor from a number of different directions.

In order to ensure that the patient is optimally treated, it is necessary to ensure that the radiation dose is deposited primarily within the tumor volume, rather than in the surrounding tissue or organs. It has been found to be problematic to quickly and reliably determine an optimization so as to maximize the dose delivery to the tumor site while minimizing radiation dose delivery to other organs or tissues.

A fast optimization algorithm is important, not only for designing good radiation treatment plans, but also for the successful implementation of future interactive adaptive treatment techniques. Conventional optimization algorithms using numerical searches, such as the known conjugate gradient search with positive beam weight constraints, usually require many iterations involving long computation times and may result in sub-optimal plans due to trapping in local minima of the objective function.

It is possible to determine a direct solution of the inverse problem using conventional quadratic objective functions, without imposing positive beam weight constraints. This solution is computationally faster but results in unrealistic (negative) beam intensities. Once an ad-hoc condition requiring the beam intensities to be positive is introduced (i.e., by forcing negative intensity values to be zero), the solution of the quadratic objective function by linear algebraic equations yields a radiation therapy dose distribution with significant artifacts. These artifacts may significantly deteriorate an otherwise optimized dose delivery. Accordingly, rather than treat a patient with a sub-optimal dose delivery, the rather more computationally intensive numerical searching has been preferred for finding the minimum of the objective function.

A further drawback of current IMRT plan optimization, is that only about seven to eleven different gantry angles may be employed because present techniques find it too computationally intensive to optimize the objective function for a greater number of beams.

In view of the above shortcomings of existing systems, it is desired to provide a method and system for optimized dose delivery, which addresses or ameliorates one or more of the mentioned shortcomings.

SUMMARY OF THE INVENTION

In one aspect, the invention provides a method of dose delivery of radiation. The method comprises the step of determining an objective function to be used for mapping radiation beams to a body volume comprising at least one target volume, and at least one non-target volume. The objective function comprises a first term related to the at least one target volume and a second term related to the at least one non-target volume. The method further comprises determining a minimum of the objective function whereby beams mapped so as to pass through the at least one non-target volume are limited such that the second term is zero only if the weights of beamlets passing through the at least one non-target volume are zero. Radiation is delivered based on the determined minimum of the objective function.

In another aspect, the invention provides a method of determining an objective function to be used for mapping radiation beams for a body volume comprising at least one target volume and at least one non-target volume. The objective function comprises a first term related to the at least one target volume and a second term related to the at least one non-target volume. The method comprises determining a minimum of the objective function whereby beams mapped so as to pass through the at least one non-target volume are limited such that the second term is zero only if intensities of beamlets passing through the at least one non-target volume are zero.

In a further aspect, the invention provides a method of providing radiation, comprising determining an objective function for optimizing radiation dose delivery to a target volume, the objective function having a symmetry term for enabling symmetrical dose delivery about an axis of the target volume, and providing radiation based on the objective function.

In yet a further aspect, the present invention provides a system for optimizing dose delivery of radiation. The system comprises computer processing means for determining an objective function to be used for mapping radiation beams to a body volume comprising at least one target volume, and at least one non-target volume, the objective function comprising a first term related to the at least one target volume and a second term related to the at least one non-target volume. The computer processing means is arranged to determine a minimum of the objective function whereby beams mapped so as to pass through the at least one non-target volume are limited such that the second term is zero only if the weights of beamlets passing through the at least one non-target volume are zero. The system further comprises data communication means operably associated with the computer processing means for providing data to a radiation delivery apparatus for delivering radiation to the body volume based on the determined minimum of the objective function.

In a still further aspect, the invention provides computer readable storage having stored thereon computer program instructions executable on a computer system for causing the computer system to perform a dose optimization method. The dose optimization method comprises determining an objective function to be used for mapping radiation beams for a body volume comprising at least one target volume and at least one non-target volume, the objective function comprising a first term related to the at least one target volume and a second term related to the at least one non-target volume; and determining a minimum of the objective function whereby beams mapped so as to pass through at least one non-target volume are limited such that the second term is zero only if intensities of beamlets passing through the at least one non-target volume are zero.

In the above aspects, it is preferred that the radiation delivery be by IMRT or Tomotherapy.

Advantageously, embodiments of the invention enable the objective function to be minimized according to the solution of a set of linear algebraic equations. While there are a number of ways to solve a system of linear equations, the preferred method is based on determining the inverse of a beamlet intersection matrix. Because of the method of determining the minimum of the objective function described herein, determining the inverse of the beamlet intersection matrix greatly reduces the possibility of generating anomalous negative beam weights for the beamlets. Accordingly, the problems associated with negative beam weights and the constraints imposed on optimization methods to avoid them may be obviated.

Further advantageously, because the technique employed by the invention allows the optimization to be framed as a solution of algebraic linear equations, the lengthy processing time required to search for the global minimum of the objective function is substituted with a significantly improved processing time. This increase in processing efficiency is measurable in orders of magnitude. For example, the present technique can accomplish in seconds or minutes what would take several hours with some prior art techniques. Accordingly, with methods and systems according to the invention, medical staff can greatly reduce the time required for radiation therapy planning while providing a highly optimal dose delivery plan.

Further advantageously, embodiments of the invention enable a larger number of radiation delivery angles to be employed, compared with previous IMRT techniques. This is due to the high computational efficiency with which the optimization is carried out according to the invention, providing higher quality conformal dose distributions to the tumor site and better quality optimizations in avoiding radiation delivery to organs at risk and other organs or tissues not forming part of the target site.

These and further features of aspects and embodiments of the invention will be described in detail in the following detailed description.

DETAILED DESCRIPTION OF THE INVENTION

Figure 1:
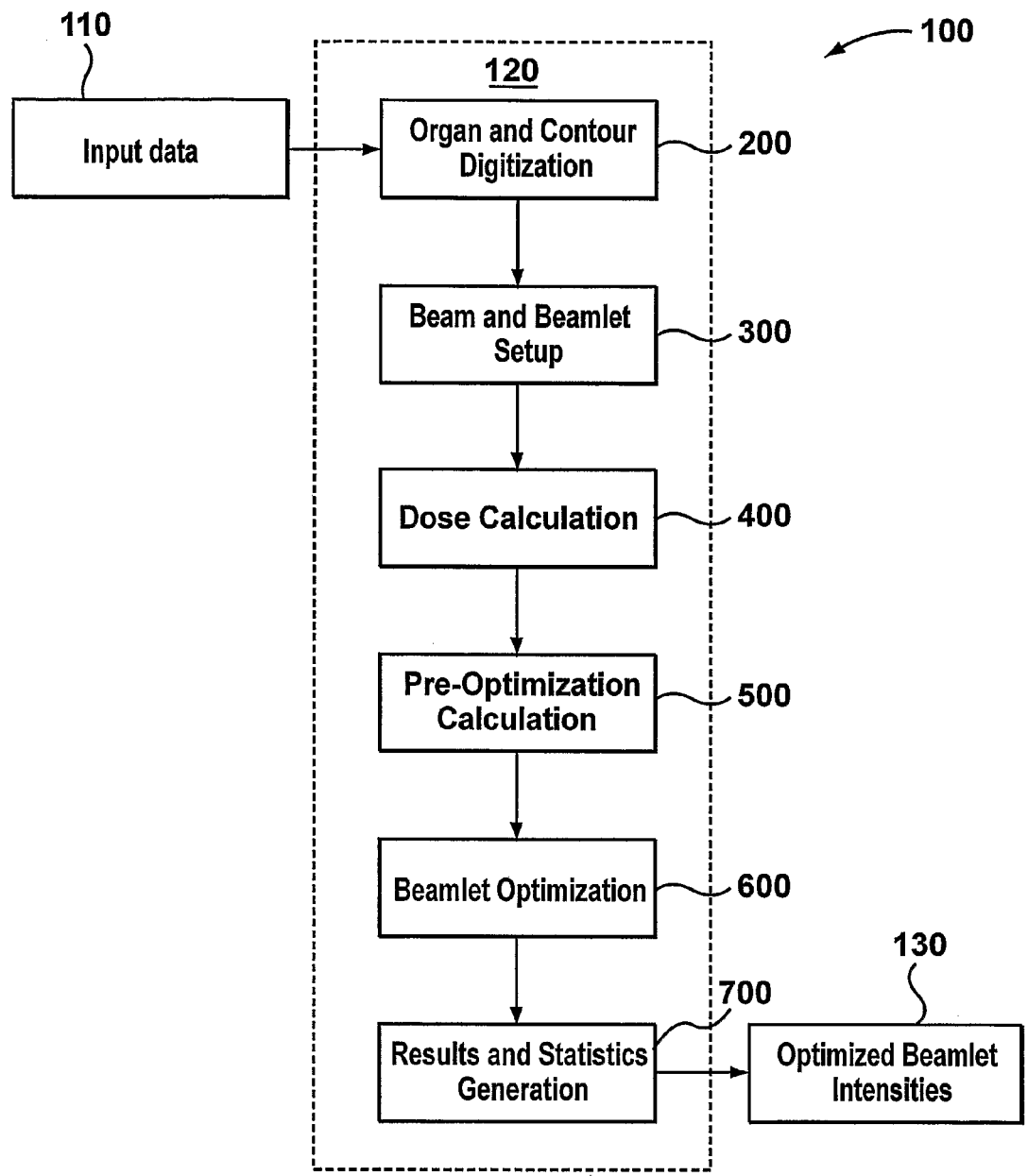
FIG. 1 is a flow chart of an overall process used in dose delivery optimization according to an embodiment of the invention.

The present invention generally relates to methods and systems for optimizing dose delivery of radiation therapy to tumor sites within a patient. Typically, the radiation will be directed toward a single tumor site, although it is not uncommon for multiple tumor sites to be treated simultaneously. While embodiments of the present invention are capable of taking into account multiple tumor sites, which are encompassed by the planning target volume (PTV), for simplicity of description, embodiments will primarily be described as they apply to a single PTV. Similarly, only a single organ at risk (OAR) and a single volume of other intervening tissues or organs, which is called herein all-the-rest (ATR), are described.

The number of PTV, OAR and ATR volumes, as well as the size and relative orientation thereof, will vary from patient to patient and according to the desired treatment plan determined by the radiation oncologist. For example, it is possible that the optimization may not have to take account of an organ at risk, or the PTV may be entirely within the organ at risk, with very little ATR volume to take account of.

It will usually be necessary or at least advisable for the supervising radiation oncologist or other suitably qualified medical personnel to determine one or more importance parameters in the objective function by which relative importance may be attributed to certain tissue or organ volumes within the patient relative to the other volumes.

During radiation dose delivery, radiation scattering commonly occurs due to the passage of the radiation through the body volume. In this application, scattering effects are not addressed in the optimization method and system. It will be understood that embodiments of the invention can be modified to account for scattering effects.

The most fundamental requirements of a radiation treatment optimization are: (i) the dose is homogeneously deposited in the PTV; (ii) the dose deposited in any OAR does not exceed a threshold value and ideally should be zero; (iii) the dose deposited in ATR organs and tissue not included in the PTV and OARs, should be as small as possible and ideally zero to minimize the risk of secondary carcinogenesis; (iv) the dose gradient crossing the PTV boundaries should be as high as possible.

Optimizations are pursued by the minimization of a positive-definite objective function, also sometimes termed a "cost function". A successful optimization will yield a global minimum to this objective function in a short computation time with physically achievable beamlet intensities (i.e. greater than or equal to zero).

The optimized objective function should minimize the dose deposited in the ATR and the OARs. Theoretically, the dose in these should be zero, although it can never actually be zero in the ATR. Consider a simplified example of two beamlets only, one with weight a and the other with weight b. The terms in the traditional optimization function for the ATR and the OAR are each of the form:

$$p(a+b)^2,$$

where p is the importance parameter of the term. The optimization searches then for the minimum:

$$\min\{(a+b)^2\},$$

The minimum is zero and it occurs for a=−b. In other words, one of the weights will be negative. This is the result from the solution of a linear system of equations.

The minimum corresponds to:

$$\frac{\partial}{\partial a}(a+b)^2 = 0$$
$$\frac{\partial}{\partial b}(a+b)^2 = 0$$

which results in a+b=0.

The current approach is then to solve instead:

$$\min\{(a+b)^2\} \text{ with the constraints } a>0, b>0.$$

This can only be solved through a numerical search. In order to address this problem, embodiments of the invention use instead a term of the form:

$$p(a^2+b^2)$$

This term cannot be zero by one beamlet having a negative intensity to cancel the other. For this term to be zero, each beamlet intensity must be zero.

The system of equations is obtained from:

$$\frac{\partial}{\partial a}(a^2+b^2) = 0$$
$$\frac{\partial}{\partial b}(a^2+b^2) = 0$$

that results in $$a=0$$
$$b=0$$

at the minimum. For a quadratic optimization function, there is only one minimum, which is the absolute minimum.

A typical objective function O satisfying the optimization conditions stated above is of the form:

$$O = p_{PTV}O_{PTV} + p_{OAR}O_{OAR} + p_{ATR}O_{ATR}$$

where the $p_k$ are importance coefficients (also called importance parameters) and the objectivity terms are:

$$O_{PTV} = \sum_{x \in PTV} \left( \sum_{i}^{all\text{-}beamlets} w_i d_i(x) - d^{PTV} \right)^2,$$

$$O_{OAR} = \sum_{x \in OAR} \left( \sum_{i}^{all\text{-}beamlets} w_i d_i(x) \right)^2,$$

$$\text{and } O_{ATR} = \sum_{x \in ATR} \left( \sum_{i}^{all\text{-}beamlets} w_i d_i(x) \right)^2,$$

where $w_i$ is the weight of beamlet i, $d_i$ is the dose deposited at destination point x by beamlet i and $d^{PTV}$ is the dose prescribed to the PTV.

The main reason for the appearance of negative weights upon optimization of the objective function O is the fact that it is usual to require the satisfaction of two conflicting demands: on one hand it is required that O ATR=0 and on the other hand it is necessary for radiation to pass through the ATR (and possibly OARs) to reach the PTV. A better requirement is that $O_{ATR}$ should be zero only if the weights of all the beamlets passing through the ATR are zero, as described in the simplified example above. This requirement is satisfied if instead of $O_{ATR}$ we use a new ATR term of the form:

$$\tilde{O}_{ATR} = \sum_{x \in ATR} \sum_{i}^{all\text{-}beamlets} w_i^2 d_i^2(x).$$

Similarly for the OAR:

$$\tilde{O}_{OAR} = \sum_{x \in OAR} \sum_{i}^{all\text{-}beamlets} w_i^2 d_i^2(x).$$

The PTV term in the objective function O cannot be written in this way. Accordingly, the medical personnel performing the optimization needs to set an importance parameter large enough on the ATR and OAR terms to balance the PTV term. Even small values of importance parameters for the OAR and ATR have been found to be sufficient.

In a preferred embodiment, a term is added to the objective function O that replaces the unrealistic zero-limit for the beamlet weights with an equal-weight limit (which will be referred to herein as circular symmetry), which is usually the initial set of weights before optimization. This term can assume different forms, as part of a general family of symmetry terms. This term can be in one of the forms:

$$O_{SYM} = \sum_{i}^{all\text{-}beamlets} (w_i - 1)^2$$

$$\text{or } O_{SYM} = \sum_{i}^{all\text{-}beamlets} (w_i^2 - w_i)$$

$$\text{or } O_{SYM} = \sum_{i}^{all\text{-}beams} \left[ \left( \sum_{j}^{\substack{all\text{-}beamlets \\ inside\ beam\ i}} w_j \right) - 1 \right]^2$$

$$\text{or } O_{SYM} = \sum_{i}^{all\text{-}beamlets} w_i^2$$

$$\text{or } O_{SYM} = \sum_{x \in \text{all-contours}}^{\text{all-beamlets}} \sum_{i} w_i^2 d_i^2(x)$$

$$\text{or } O_{SYM} = \sum_{\substack{x \in \text{all-contours} \\ \text{except PTV}}}^{\text{all-beamlets}} \sum_{i} w_i^2 d_i^2(x)$$

or other forms satisfying the condition in the next section. In the following we will use, for illustration, the first form of $O_{SYM}$.

With the weights normalized to:

$$\sum_{i}^{\text{all-beamlets}} w_i = \text{total number of beamlets,}$$

$O_{SYM}$ is positive and its minimum is zero when $w_i=1$ for all i.

The objective function O then becomes:

$$\tilde{O} = p_{PTV} O_{PTV} + p_{OAR} \tilde{O}_{OAR} + p_{ATR} \tilde{O}_{ATR} + p_{SYM} O_{SYM}$$

The underlying approach behind current optimization techniques is to start from zero weights and analyze the results as the weights of each beamlet are increased. As a result, searches for a minimum do not necessarily result in symmetric dose depositions, even when the system treated may have a symmetry (eg. symmetric under a reflection). The symmetry term introduced here, in essence, starts the analysis of the weights from the opposite end: with all beams having the same weight. Given that the radiation source travels around the isocentre (i.e. the designated centroid of the form or volume) describing a circle on each slice, this requirement starts the analysis from a circularly symmetric perspective.

The circular symmetry term $O_{SYM}$ has been found to introduce a high degree of stability in the results, even when coupled with a small importance parameter $p_{SYM}$. Moreover, it tends to smooth the dose distribution within the body volume, avoiding local hot or cold spots.

This introduced symmetry term provides a significant bias against generation of negative beamlet intensities during minimization of the objective function using matrix inversion. This can be observed if, for example, all importance parameters apart from $p_{SYM}$ are zero. In such a case, the optimization of the objective function would yield a plan where all beamlets have the same unit weight. Thus, a non-zero value for $p_{SYM}$ biases the beamlet weights towards a unit weight distribution. This bias is small for small values of $p_{SYM}$ and is stronger for larger values. If one were to iteratively test and observe the beamlet weight distribution, starting with a large value of $p_{SYM}$ and decreasing it in steps, the distribution would resolve from one in which all weights are substantially the same to a distribution in which the beamlet weights are substantially optimized, while keeping all beamlet weights positive.

An advantageous effect of the symmetry term in the objective function is that, for a contour having a point or axial symmetry around the isocentre, the beamlet weight distribution (and hence dose deposit) as a function of gantry angles, will closely follow that symmetry. This ability to follow symmetries is derived in part from the large number of gantry angles which can be accommodated in the optimization method described herein and translates into an ability to provide high quality conformal dose deposit mapping for target volumes in general.

With the symmetry term included, a simplified form of the new objective function can be expressed as:

$$\tilde{O} = \sum_{k}^{\substack{\text{all organs with} \\ \text{required dose}}} p_k^{dose} O_k^{dose} + \sum_{n}^{\substack{\text{all organs without} \\ \text{required dose}}} p_n^{no\text{-}dose} \tilde{O}_n^{no\text{-}dose} + p_{sym} O_{sym}$$

where $$O_k^{dose} = \sum_{x \in \text{organ}_k} \left( \sum_{i}^{\text{all beamlets}} w_i d_i(x) - d^{\text{organ}_k} \right)^2$$

where $d^{\text{organ}_k}$ is the dose prescribed to organ k, and $$\tilde{O}_n^{no\text{-}dose} = \sum_{x \in \text{organ}_n} \sum_{i}^{\text{all-beamlets}} w_i^2 d_i^2(x)$$

The optimal set of weights is obtained by minimizing the objective function. The minimum occurs when $$\frac{\partial O}{\partial w_j} = O \text{ for all } w_j$$

$$\text{or } \frac{\partial O}{\partial w_j} = \sum_{k}^{\substack{\text{all organs} \\ \text{with reqired dose}}} p_k^{dose} \frac{\partial O_k^{dose}}{\partial w_j} +$$

$$\sum_{n}^{\substack{\text{all organs} \\ \text{without required dose}}} p_n^{no\text{-}dose} \frac{\partial \tilde{O}_n^{no\text{-}dose}}{\partial w_j} + p_{sym} \frac{\partial O^{sym}}{\partial w_j} = 0$$

where $\frac{\partial O_k^{dose}}{\partial w_j} = 2 \sum_{i}^{\text{allbeamlets}} w_i \left( \sum_{x \in \text{organ}_k} d_i(x) d_j(x) \right) - 2 d^{\text{organ}_k} \sum_{x \in \text{organ}_k} d_j(x),$ $\frac{\partial O_k^{dose}}{\partial w_j} = 2 \sum_{i}^{\text{allbeamlets}} w_i \left( \sum_{x \in \text{organ}_k} d_i(x) d_j(x) \right) - 2 d^{\text{organ}_k} \sum_{x \in \text{organ}_k} d_j(x),$ $\frac{\partial \tilde{O}_n^{no\text{-}dose}}{\partial w_j} =$ $$2 w_j \left( \sum_{x \in \text{organ}_n} d_j^2(x) \right) = 2 w_j \sum_{i}^{\text{allbeamlets}} \left[ w_i \left( \sum_{x \in \text{organ}_k} d_i(x) d_j(x) \right) \times \delta_{ij} \right]$$

and $\frac{\partial O^{sym}}{\partial \omega_j} = 2(\omega_j - 1) = 2 \left[ \left( \sum_{i}^{\text{allbeamlets}} \omega_i \times \delta_{ij} \right) - 1 \right]$ where $\delta_{ij}$ is a unit matrix (i.e., a square array with all elements zero except for the diagonal elements that are all equal to one).

Calling now $$\alpha_{ij}^{organ_k} = \sum_{x \in organ_k} d_i(x) d_j(x)$$

and $$\beta_j^{organ_k} = d^{organ_k} \sum_{x \in organ_k} d_j(x),$$

then for each beamlet across the whole body volume:

$$\alpha_{ij} = \overset{\text{all organs}}{\underset{\text{with required dose}}{\sum_k}} p_k^{dose} \alpha_{ij}^{organ_k} + \overset{\text{all organs}}{\underset{\text{without required dose}}{\sum_n}} p_n^{no\text{-}dose} \alpha_{ij}^{organ_n} \delta_{ij} + p_{sym} \delta_{ij}$$

and $\beta_i = \overset{\text{all organs}}{\underset{\text{with required dose}}{\sum_k}} p_k^{dose} \beta_i^{organ_k} + p_{sym}$ With the noted modifications to the objective function, the optimization problem for all the beamlet intensities is reduced to the solution of a linear system of equations of the form:

$$\sum_j^{allbeamlets} \alpha_{ij} w_j = \beta_i \quad (1)$$

where $w_j$ is the (unknown) weight or intensity of beamlet j, $\beta_j$ is a vector (referenced herein as the beamlet dose deposit vector or array) of coefficients that depends on the dose deposited by beamlet i within the PTV, and $\alpha_{ij}$ is a matrix (referenced herein as the beamlet intersection matrix) that describes the product of the doses deposited by the intersecting pairs of beamlets i and j on all organs.

The set of optimal beamlet weights is obtained, for example, from (1) by inversion:

$$\omega_i = \sum_j^{allbeamlets} \alpha_{ij}^{-1} \beta_j$$

Thus, the solution to the (large) system of linear equations (1) can be obtained quickly and accurately by inverting the matrix $\alpha_{ij}$ using standard matrix inversion routines and summing the product of inverted matrix $\alpha_{ij}^{-1}$ with vector $\beta_j$ for each beamlet j.

In one embodiment, the importance parameters for each region can be generalized to be region-dependent, i.e. to have different values in a region within a contour, in which case they can be of the form $$p_{region_k} = \hat{p}_{region_k} q_{region_k}(x)$$

where $\hat{p}$ is an overall constant and $q(x)$ is a function of position.

In this case, the definitions of the arrays $\alpha$ and $\beta$ may be generalized by $$\hat{\alpha}_{ij}^{region_k} = \sum_{x \in region_k} q_{region_k}(x) d_i(x) d_j(x)$$

and $$\hat{\beta}_j^{region_k} = d^{region_k} \sum_{x \in region_k} q_{region_k}(x) d_j(x)$$

Using these definitions, the matrix formulation of the optimization process now becomes:

$$\hat{\alpha}_{ij} = \hat{p}_{PTV} \hat{\alpha}_{ij}^{PTV} + (\hat{p}_{OAR} \hat{\alpha}_{ij}^{OAR} + \hat{p}_{ATR} \alpha_{ij}^{ATR} + p_{sym}) \delta_{ij}$$

$$\hat{\beta}_j = \hat{p}_{PTV} \hat{\beta}_j^{PTV} + p_{sym}.$$

The previous linear system of equations is now $$\sum_i w_i \hat{\alpha}_{ij} = \hat{\beta}_j$$

and the optimized solution is obtained by the inversion:

$$w_i = \sum_j \hat{\alpha}_{ij}^{-1} \hat{\beta}_j$$

If the functional dependence of the importance coefficients remains unaltered, a search of the best set of importance parameters is reduced to a search of the best set $\hat{p}_{region_k}$ in which case the arrays $\hat{\alpha}_{region_k}$ and $\hat{\beta}_{region_k}$ do not need to be recalculated. Matrices $\alpha_{ij}$ and $\beta_{ij}$ are obtained from the matrices $\hat{\alpha}_{ij}$ and $\hat{\beta}_{ij}$ by simply setting $q_{region_k}=1$ for all regions, returning to the case in which the importance coefficient has a unique value within a contour.

Turning now to the drawings, FIG. 1 is a block diagram illustrating an optimization process 100 according to an embodiment of the invention. The optimization process 100 involves obtaining scanned input data 110 from a scanning apparatus which outputs a series of scans, for example such as computed tomography (CT) scans. This scanned input data includes a series of "slices" through the body. Each of these slices shows a part of the tumor volume in cross-section, together with the remaining body volumes, including any organs at risk. When these slices are aggregated as a series of parallel slices, a three-dimensional picture of the target tumor volume and other body volumes can be obtained. Accordingly, the input data 110 includes data concerning a number of such parallel slices, sufficient to describe the body volume, including the PTV, to which radiation will be directed. The input data 110 may be in the Dicom RT standard file format (including standardized radiation therapy-specific data objects), which can be generated by most CT scanning systems or other treatment planning systems. Further details of the Dicom RT standard can be obtained from the National Electrical Manufacturers Association (NEMA).

The input data 110 is received by an optimization module 120, which processes this input data, as described further in relation to FIGS. 2 to 7. Once the optimization module 120 has processed the input data 110, an output file 130 of the optimized beamlet intensities is generated and output to a radiation dose delivery apparatus, such as a medical linear accelerator, through a suitable Dicom RT protocol. The radiation therapy can then be delivered according to the optimized dose delivery.

Output file 130 is formatted so as to provide sequencing data for mapping the optimized beamlet intensities to the leafs of a multi-leaf collimator. This is done according to existing leaf sequencing algorithms.

The scan data 110 can be stored (eg., in memory 20, shown in FIG. 8) and used to perform several dose optimizations over a period of time, as the optimization process facilitates adaptive adjustment of dose delivery planning based on different user input requirements.

Optimization module 120 is comprised of a series of computer program instructions aggregated to form a software program executable by a computer system (such as computer system 12 in FIG. 8, described later). Optimization module 120 is configured to receive the scan data input 110 in a known file format (e.g., Dicom RT) and to provide the optimized beamlet intensities in output file 130 in a corresponding known file format.

Optimization module 120 executes a number of sequential steps, grouped as several sets of steps, which are referred to as subprocesses, as part of the overall optimization process 100. These subprocesses include organ and contour digitization 200, beam and beamlet setup 300, dose calculation 400, pre-optimization calculation 500, beamlet optimization 600 and results and statistics generation 700. These subprocesses are described in further detail below, with reference to FIGS. 2 to 7.

Figure 2:
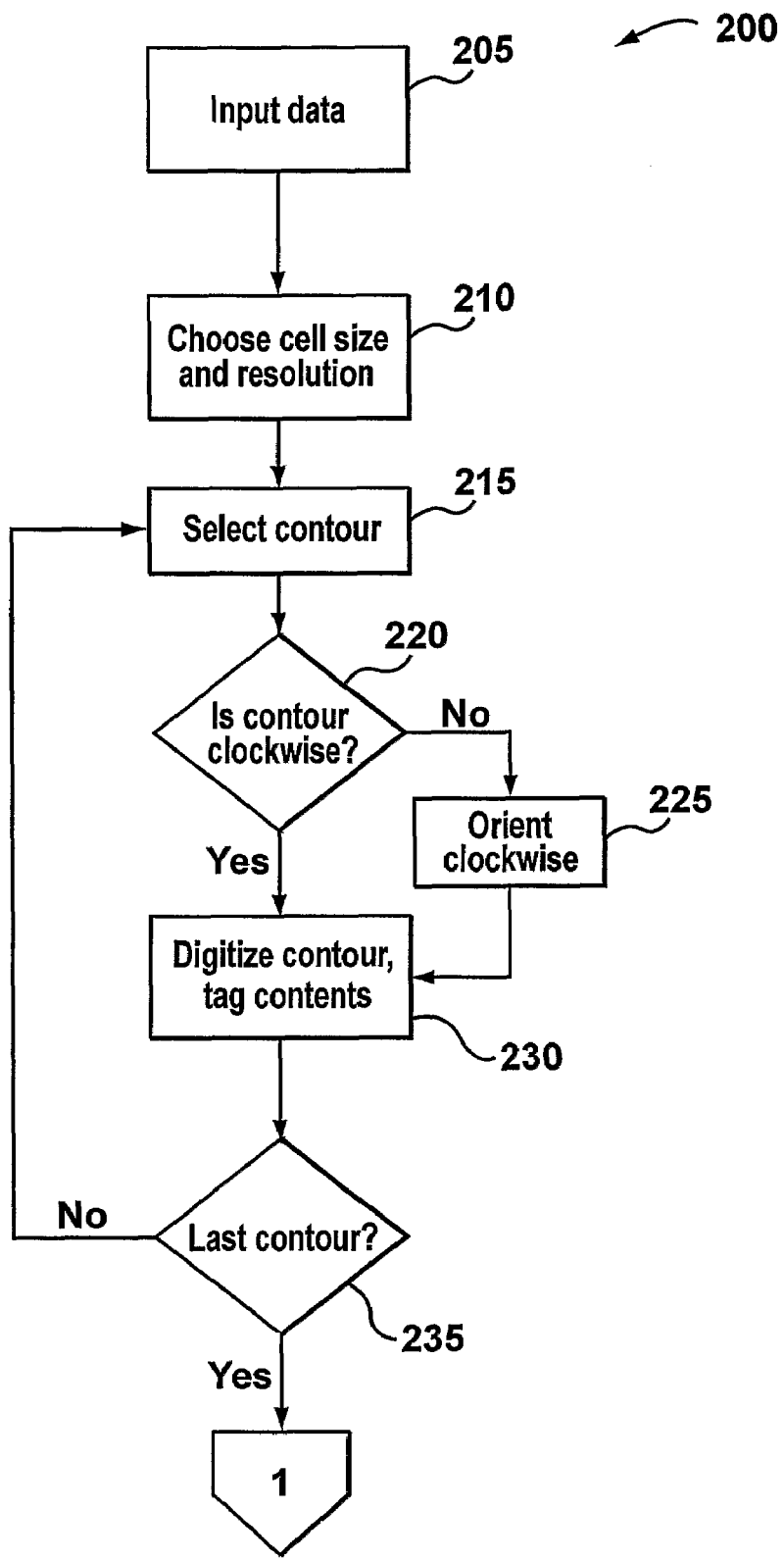
FIG. 2 is a flow chart of an organ and contour digitization sub-process of the overall process shown in FIG. 1.

Referring now to FIG. 2, organ and contour digitization subprocess 200 is described in further detail. Organ and contour digitization subprocess 200 handles the input of contour data from the CT scans and digitizes the contours so as to map them onto an underlying grid of cells to which all parts of the body volume shown in the CT scan are mapped. Subprocess 200 establishes a main array for storing data for all of the cells in the body for each CT slice. Subsets of the elements of the main array are also stored, corresponding to all of the contours within the body, such as the PTV and OAR.

At step 205, the input data 110 is received as input to the optimization module 120. The input data 110 received in this respect includes information including, for example, the treatment type (eg. Tomotherapy, IMRT) to be performed, the required dose to be deposited within the PTV, the dose-volume constraints and the CT scans, including organ contours, determined by the radiation oncologist. The dose-volume constraints indicate the maximum or minimum radiation dose to be delivered to a particular volume. For example, for an organ at risk such as the spinal cord, a constraint may be provided such that no more than 45 Gy of radiation dose should be received in any part of the OAR volume.

Once the input data 110 is received at step 205, supervising medical personnel may choose, at step 210, the grid cell size and resolution to be used for optimizing the radiation dose delivery. This information is then used to generate a discretized grid having cells of the chosen size. For each CT scan, all organs, contours and beams are mapped onto a single main array representing grid cells of the chosen spatial size within the body volume. Arrays representing cells with each organ contour, beam and beamlet are subsets of this main array. Each element of each array includes the grid coordinates of the corresponding cell in the grid. A typical cell size employed by embodiments of the invention may be 1 mm square in the plane of each slice.

The properties of an organ are assumed to be uniform within each cell. Within the descretized grid, beam propagation is calculated with an accuracy given by the resolution, which is usually about 1.25 times the width (which equals the height) of each cell.

Importantly, the resolution is set greater than the cell size so that each beamlet always traverses at least the center of one cell in the grid at each depth level of its propagation. This condition produces beamlets that are more regular in shape and avoids the beamlets being discontinuous with adjacent beamlets. Within each step and within a width equal to the resolution, the beam properties are assumed to be uniform.

Because of the higher computational efficiency enabled by embodiments of the invention, more data can be handled by the optimization process 100 and a relatively high resolution and small cell size can be achieved for the cells of the PTV, OAR and ATR volumes, leading to a more optimized treatment plan for the patient.

At step 215, a contour of the PTV is retrieved from the Dicom RT input data 110. At step 220, the contour is checked for clockwise or counter-clockwise orientation. If the points of the contour are in a counter-clockwise order, the order of those points is reversed so as to be clockwise at step 225. If the points of the contour are in a clockwise order, the contour is digitized so as to interpolate a continuous contour outline from contour points provided by the radiation oncologist and the cells within the contour are tagged and saved as such, at step 230.

The method for determining the orientation of the contour is as follows. Each slice of each organ is represented by a two-dimensional contour in the plane of that slice. Here we refer to the two-dimensional contours in a specific slice. For each contour, the input data specifies a set of points or vertices (e.g. x-y coordinates) that outline that contour. These vertices are generated by the radiation oncologist on the basis of CT scan images. In order to be able to find which points are inside or outside that contour, it is necessary to first find out if the set of vertices follows a clockwise or anticlockwise direction.

Assuming a set of orthogonal axes defined in the plane of the slice:
1) Find vertex A: the topmost vertex in the contour.
2) Find vertex C: the bottom vertex in the contour.
3) Find vertex B: the rightmost vertex in the contour that is neither A or C.
4) Find vertex D: the leftmost vertex in the contour that is neither A or C.

Given that the contour encloses a finite area, at least three of the above vertices must be distinct. If the contour is in the clockwise direction, then any three distinct vertices of the above must be in the order A-B-C-D (or any cycle of this order, such as D-A-B-C). If it is not, then the contour is determined to be in an anticlockwise orientation and the order of the elements of the contour array is inverted to assume clockwise order.

After step 225 or 220, digitizing is performed at step 230, starting from the topmost vertex and proceeding clockwise to join each consecutive pair of vertices by lines. The area inside the contour is effectively divided into horizontal lines, each starting at the left boundary and ending at the right boundary. As these lines are drawn between vertices, the lines are digitized into cells or "pixels" which are inserted in the main array into which all contours are digitized.

In broad terms:
1) If the line is drawn in a direction going downwards, then each pixel on that line is a right boundary of the horizontal line at the height of the pixel.
2) If the line is drawn in a direction going upwards, then each pixel on that line is a left boundary of the horizontal line at the height of the pixel.
3) The position of all left and right boundaries for each line at each height within a contour is stored in memory.
4) After the boundary has been completely digitized, all of the cells are labeled in each horizontal line between the saved left and right boundaries as belonging to the surface enclosed by the relevant contour.

At step 235, it is determined whether the last contour has been digitized. Steps 215 to 235 are repeated for each contour and for each organ volume (eg. OAR, ATR, PTV). Once the last contour has been digitized, organ and contour digitization subprocess 200 feeds into beam and beamlet setup subprocess 300 at step 305, as indicated by reference indicator 1 in FIGS. 2 and 3.

Figure 3:
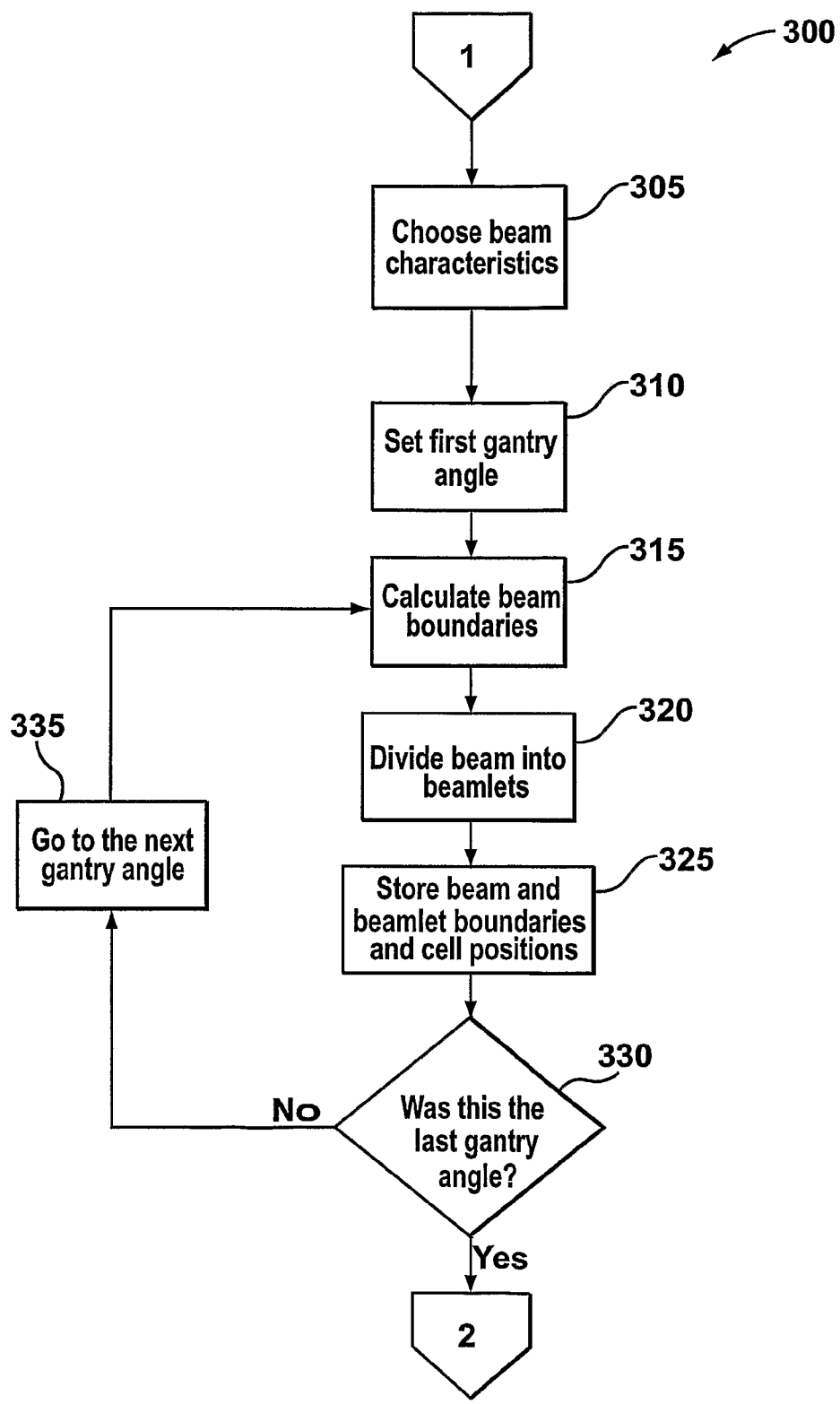
FIG. 3 is a flow chart of a beams and beamlets set-up sub-process of the process shown in FIG. 1.

Referring now to FIG. 3, beam and beamlet setup subprocess 300 is described. Beam and beamlet setup subprocess 300 determines the boundaries of each beam as projected from each different angle toward the PTV. Subprocess 300 divides the beams into beamlets, calculates the beamlet boundaries and determines which cells are inside each beamlet for each beam.

Subprocess 300 begins with data input from the user (i.e. medical personnel planning the optimized dose delivery) as to the desired radiation beam characteristics, at step 305. For example, for IMRT, multiple beams (for example, up to 51) may be specified at various angles relative to the PTV isocentre. At this step, the user also inputs beam setup information, such as the distance between the radiation source and the PTV isocentre. For Helical Tomotherapy, step 305 commonly involves choosing 51 beams at equally spaced angles, with beamlets separated by about 6.25 mm at the PTV isocentre.

For radiation therapy, the radiation beams are typically delivered to a patient lying on a bed while a gantry carrying a radiation beam emitter moves around the patient. The gantry can be positioned at numerous different angles, depending on the dose delivery plan developed by the radiation oncologist and the limitations of the radiation delivery apparatus. For IMRT, the chosen gantry angles can be along a circular arc around the patient in a single plane or in multiple intersecting planes, treating all tumor slices simultaneously, one gantry angle at a time. For Tomotherapy, each slice is treated from set gantry angles along a predetermined circular or helical arc.

Once the beam characteristics are chosen at step 305, the first of the predetermined gantry angles is set at step 310. The beam boundaries are then calculated at step 315, so as to only coincide with the outer-most edges of the PTV contour, based on the beam setup information and PTV contour data.

At each gantry angle, the position and width of the beam is calculated in order to fully cover the PTV as seen by the beam source from the radiation beam emitter.

Once the planned beam boundaries are determined at step 315, the beam is divided into beamlets at step 320. The number of beamlets within each beam will depend on the tumor-shape, gantry angle, equipment limitations, beam boundaries and previously specified resolution. Once the number of planned beamlets is determined, the positions of each of the leafs in the multi-leaf collimator are calculated for the beam from the selected gantry angle.

At step 325, for each beam and beamlet, the cells within each organ and contour through which each beam and beamlet would pass are stored. This allows quick calculation of beam statistics for each beam, as well as quick calculation of the optimization arrays for the beamlet intensities.

At step 330, subprocess 300 checks whether the last of the predetermined gantry angles has been selected, and if not, the next gantry angle is selected at step 335. Steps 315 to 325 are repeated for each gantry angle chosen at step 335.

Figure 4:
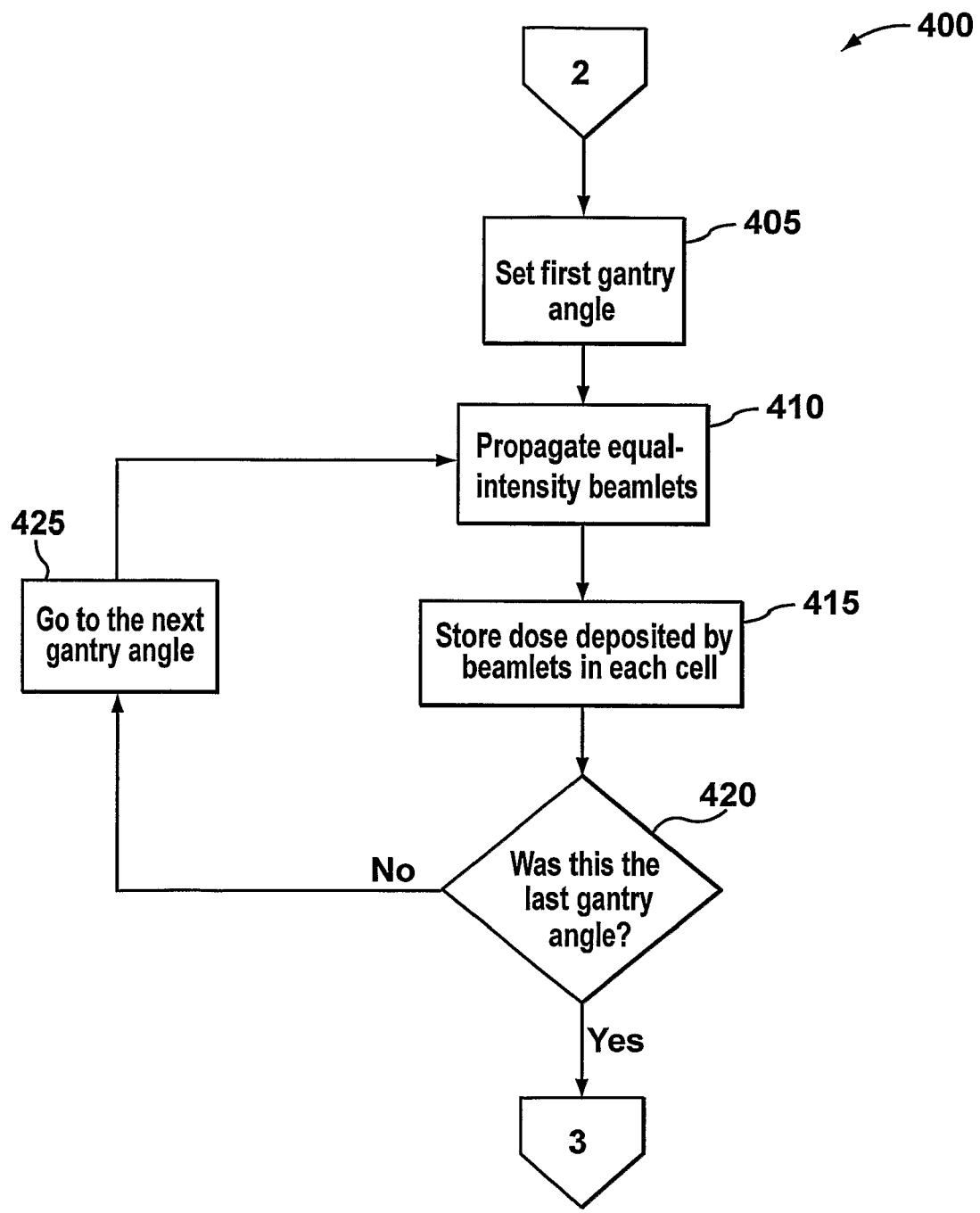
FIG. 4 is a flow chart of a dose calculations sub-process of the process shown in FIG. 1.

After the last gantry angle has been processed at step 330, subprocess 300 feeds into dose calculation subprocess 400, beginning at step 405, as indicated by reference indicator 2 in FIGS. 3 and 4.

Referring now to FIG. 4, dose calculation subprocess 400 is described. Dose calculation subprocess 400 simulates the propagation of each beamlet toward the PTV so as to determine the amount of radiation energy which would be deposited by each beamlet in each cell of each organ, based on the previously determined beam and beamlet setup. The determined dose deposit in each cell is then stored for later reference.

At step 405, the first gantry angle is selected from which beamlets are to be propagated. At step 410, equal intensity beamlets are propagated (as a simulation for planning calculation purposes only) according to the beam and beamlet setup determined in subprocess 300. The equal intensity beamlets propagated at step 410 have a default normalized weighting of 1.

For radiation therapy planning calculations, the way in which each beamlet of each beam propagates through tissue and deposits energy in each cell is calculated as follows. For the purpose of calculating beamlet propagation, each (actual) beamlet is (computationally) divided into narrower sub-beamlets, termed here "elementary propagators". The width of each of these elementary propagators (at the isocentre) is equal to the resolution (approximately 1.25 times the linear cell dimension).

The energy deposit during propagation of each elementary propagator is calculated (according to a known formula) in small steps in the direction of propagation according to the resolution. The elementary propagator is divided or resolved along its length into small trapezoids (due to divergence of the beamlets from the emitter) of linear dimension equal to the resolution (i.e. slightly larger than the linear dimension of the cells in the underlying grid). Although the linear dimension (i.e., the distance between the parallel sides) of each trapezoid is uniform, each succeeding trapezoid is slightly wider than the last, so that the trapezoids are non-uniform in size.

When the center of a cell (in the main underlying grid) lies inside one of these small trapezoids, the elementary propagator is determined to deposit energy in that cell. By making the resolution slightly larger than the linear dimension of a cell, as the elementary propagator propagates, every single trapezoid into which it is divided can be considered to deposit energy into at least one cell, thus making the elementary propagator continuous and not fragmented.

The proportion of the resolution to the cell width may vary, depending on requirements, but is preferably between 1 and 2 times the cell width.

At step 415, the dose to be deposited in each cell by the propagated beamlets is stored for each cell of each organ or body volume affected by the beamlets of the beam at the selected gantry angle.

Dose calculation subprocess 400 checks at step 420 whether the selected gantry angle is the last angle at which simulated beamlet intensities are to be propagated and, if it is not, the next gantry angle is selected at step 425 and steps 410 and 415 are repeated until the last gantry angle has been simulated.

The planned beamlet intensities stored as part of subprocess 400 are used to calculate the dose which would be deposited by each beamlet in the beam at the selected gantry angle for each cell at each volume affected by the beamlets. The dose which would be deposited by each beamlet is calculated by propagating several elementary propagators of radiation per beamlet (as described above), each propagator being of equal width (at the isocentre) to the resolution. This calculation is performed according to existing dose deposition formulae. In storage step 415, the arrays of the cell-by-cell dose deposit data of all beamlets for all organs are stored (eg. in RAM) for later use without recalculation.

Figure 5:
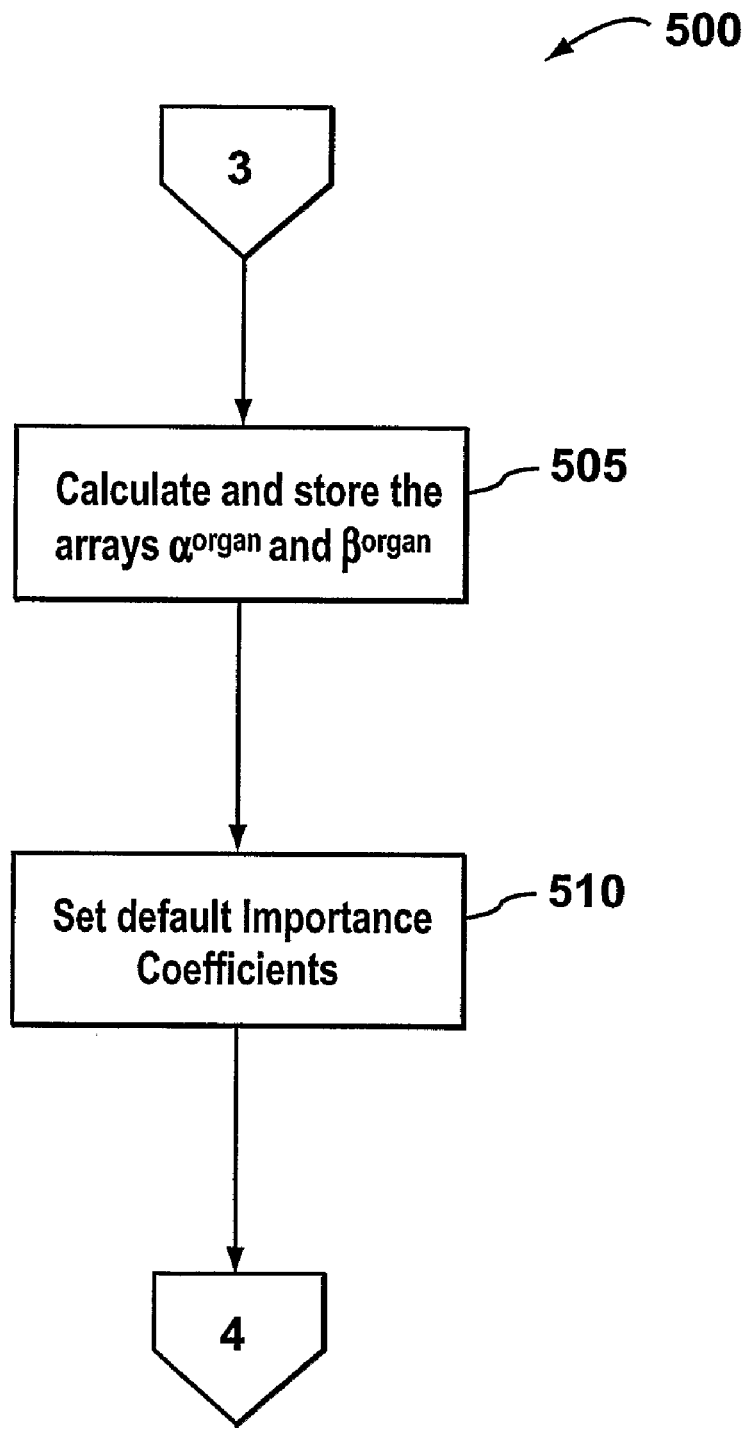
FIG. 5 is a flow chart of a pre-optimization calculations sub-process of the process shown in FIG. 1.

Dose calculation subprocess 400 feeds into pre-optimization calculation subprocess 500 in FIG. 5. Reference indicator 3 in FIGS. 4 and 5 joins the respective flowcharts in this regard.

Referring now to FIG. 5, pre-optimization calculation subprocess 500 is described. Pre-optimization calculation subprocess 500 calculates and stores the matrices and arrays of dose deposit data in each cell for each beamlet and for intersecting beamlets, in order to perform the optimization calculations.

Subprocess 500 begins with step 505, at which dose deposition coefficient arrays $\beta^{organ}$ and beamlet intersection matrices $\alpha^{organ}$ for all organs and contours are calculated and stored. Each matrix $\alpha^{organ}$ comprises elements that are the products of the doses deposited by intersecting pairs of beamlets (i.e. from different gantry angles) across all cells in an organ (i.e. PTV, ATR or OAR). Array $\beta^{organ}$ is a vector of coefficients of the dose to be deposited by each beamlet within the cells of each organ.

For each organ, k, the matrix $\alpha^{organ}$ has elements $\alpha_{ij}^{organ_k}$ labeled by the indices i and j, determined according to the expression:

$$\alpha_{ij}^{organ_k} = \sum_{x \in organ_k} d_i(x) d_j(x)$$

where the summation runs over all points x inside organ k and $d_i(x)$ and $d_j(x)$ are the doses deposited at point x by unit-weight beamlets i and j, respectively. The terms of this matrix are quickly calculated from the arrays stored in fast memory (RAM) for the unit weight beamlets in step 415.

As part of step 505, the arrays and matrices for each beamlet propagated within each organ are stored in memory (eg. RAM) for later quick retrieval during the optimization calculations. The calculations at step 505 are performed only once for the initial set of equal intensity beamlets.

At step 510, default importance coefficients for the objective function are set. These default coefficients are set according to previous experience with appropriate weighting. These coefficients are used to achieve a workable optimization of the objective function Õ. The medical physicist or other medical personnel performing the optimization may choose the default coefficients and may alter these later as part of beamlet optimization subprocess 600.

Typical default values for the importance parameters are, for example, $p_{PTV}$=40; $p_{OAR}$=28; $p_{ATR}$=1; and $p_{SYM}$=1. If a better conformal dose deposit within the PTV is needed, then $p_{PTV}$ is increased, for example to 100 or more. Similarly, the values for $p_{OAR}$ and $p_{ATR}$ are adjusted to suit radiation therapy planning requirements. If the system of contours is such that with these parameters or with the modified parameters the conditions on the PTV or the OAR are excessively demanding and one or more negative beamlet weights are detected, then one or both of $p_{ATR}$ and $p_{SYM}$ can be increased, typically to a value like 2 or 3.

Figure 6:
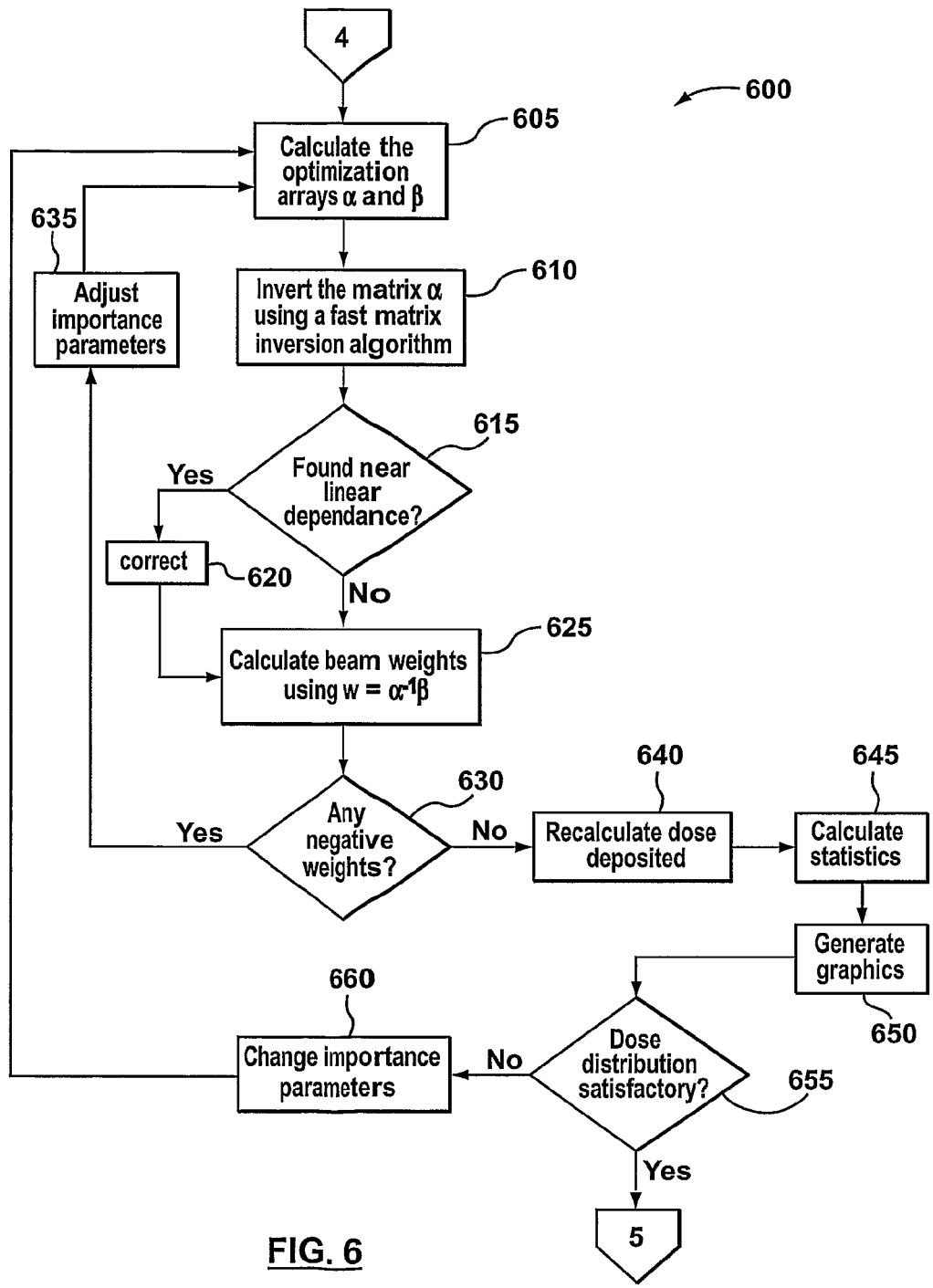
FIG. 6 is a flow chart of a beamlets optimization sub-process of the process shown in FIG. 1.

After pre-optimization calculation subprocess 500, step 510 feeds into step 605 in beamlet optimization subprocess 600. FIGS. 5 and 6 are linked by reference indicator 4 in this regard.

Referring now to FIG. 6, beamlet optimization subprocess 600 is described. Beamlet optimization subprocess 600 performs the optimization calculations by matrix inversion of the beamlet intersection matrix and determines the optimal beamlet weights according to the solution of a system of linear equations. Beamlet optimization subprocess 600 further determines the planned dose distribution among all contours and generates graphical outputs of the dose distribution.

Subprocess 600 begins with step 605, at which the overall optimization matrix $\alpha$ and array $\beta$ are calculated according to the precalculated arrays and matrices for the organs and beamlets, taking into account the predetermined importance coefficients.

Matrix $\alpha$ and array $\beta$ are calculated for each beamlet by the simple expressions:

$$\beta_i = \sum_k^{allPTV} p^{PTV_k} \beta_{iPTV_k}^{PTV_k} + p_{sym} \text{ and}$$

$$\alpha_{ij} = \sum_k^{allPTV} p^{PTV_k} \alpha_{ij}^{PTV_k} + \sum_k^{allOAR} p^{OAR_k} \alpha_{ij}^{OAR_k} \delta_{ij} + \sum_k^{allATR} p^{ATR_k} \alpha_{ij}^{ATR_k} \delta_{ij} + p_{sym} \delta_{ij}$$

where $\delta_{ij}$ is a unit matrix and k is the number of contours of each kind (eg. OAR, PTV, ATR). This is a fast calculation for which the arrays saved in fast memory in step 505 are used.

At step 610, the matrix $\alpha$ is inverted using a known fast matrix inversion algorithm, such as the lower-upper-diagonal (LUD) algorithm. Any suitably computationally efficient matrix inversion algorithm may be used at step 610.

At step 615, subprocess 600 checks matrix $\alpha$ for near-linear dependence. This check is performed to ensure that there are no redundant or nearly redundant beamlets. If near-linear dependence is found, this is corrected at step 620 using a singular value decomposition (SVD) algorithm to appropriately condition matrix $\alpha$.

In the absence of near-linear dependence, the beamlet weights are calculated, at step 625, as the product of inverted matrix $\alpha$ with dose deposit array $\beta$. As part of step 625, the optimized beamlet weights are determined according to the solution of a linear system of equations (resulting from the product of inverted matrix $\alpha^{-1}$ with dose deposit array $\beta$). This solution can be obtained by solving a system of N linear equations in N variables, where N is the number of beamlets.

At step 630, beamlet optimization subprocess 600 checks whether any of the beamlet weights have been calculated at step 625 to be negative. If there are any negative weights (i.e. negative beamlet intensities), the user is notified and, at step 635, is advised to adjust one or more of the importance coefficients in the objective function. Following adjustment of the importance coefficients, steps 605 to 625 are repeated until no negative beamlet weights are output from the calculations of step 625.

If the calculated beamlet weights are positive or zero, the optimized dose to be deposited in all organs and contours is recalculated with the optimized beamlet weights at step 640. At step 645, dose deposit statistics are calculated for all organs, contours and beamlets, including dose volume histogram (DVH) plots, for the optimized dose delivery plan.

Graphics, such as colour-coded dose distribution maps, are generated at step 650 according to the calculated dose statistics, where the colour-coded dose distribution is overlaid on the contours to provide an easy indication of the dose distribution across all contoured volumes. Example dose distribution maps and dose-volume histograms are shown in FIGS. 9A to 9D. Each colour-coded dose distribution graph is accompanied by a corresponding dose volume histogram to provide the user with a more accurate indication of whether the dose-volume constraints will be met by the proposed optimization of beamlet weights.

At step 655, the user is given the opportunity to indicate whether the planned dose distribution is satisfactory and, if not, is prompted to change the importance parameters at step 660. If the user elects to change the importance coefficients at step 660, steps 605 to 655 are re-executed until a satisfactory dose distribution is achieved.

Alternatively, if the user wishes to change some of the physical setup characteristics, such as the gantry angles, optimization process 100 returns (not shown) the user to subprocess 200 or 300, as appropriate.

Figure 7:
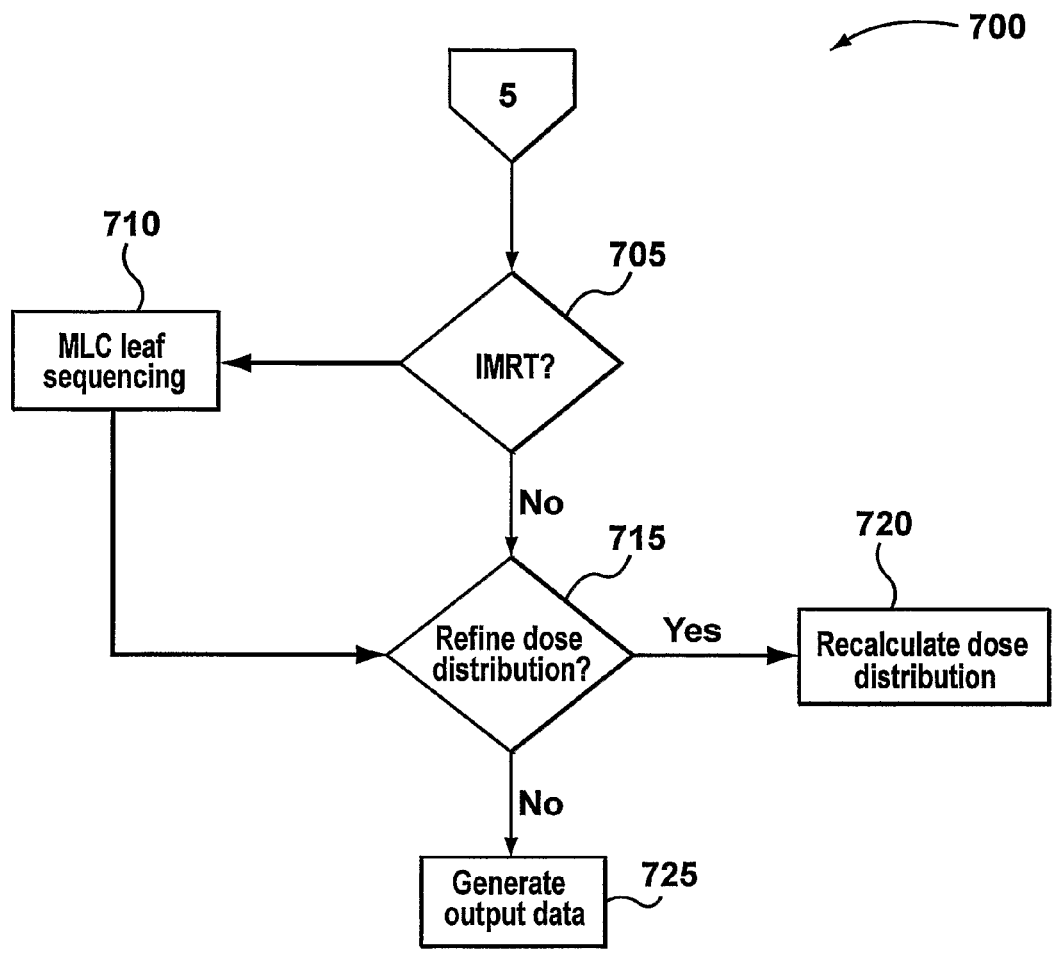
FIG. 7 is a flow chart of a results and statistics output sub-process of the process shown in FIG. 1.

Once the dose distribution is considered to be satisfactory, beamlet optimization subprocess 600 feeds into step 705 of result and statistics generation subprocess 700. FIGS. 6 and 7 are joined by reference indicator 5 in this respect.

Referring now to FIG. 7, results and statistics generation subprocess 700 is described. Results and statistics generation subprocess 700 generates an output of the optimized beamlet weights after the planned dose distribution is approved or refined.

At step 705, it is determined whether the desired form of radiation therapy is IMRT, and if so, generates leaf sequencing data for a multi-leaf collimator (MLC), at step 710. If the desired form of radiation therapy is Tomotherapy, a beam profile of collimated beamlets is generated (not shown) for each beam at each gantry angle and for each tumor slice.

At step 715, the user is again given the opportunity to refine the dose distribution, for example in order to suit the MLC leaf sequencing (if IMRT is used) or to accommodate other physical constraints imposed by the radiation therapy delivery system. If the dose distribution requires refining, a more accurate dose deposition may be substituted for that previously defined and the dose distribution is recalculated at step 720.

If no further refinement of the dose distribution is required, an output data file is created at step 725, including optimized beamlet intensities 130 and leaf positions and sequences generated at step 710. Any beam, organ or contour statistics, together with data for displaying colour-coded dose distributions and dose-volume histograms may also be output (eg. to a display) at step 725, if desired. The statistics and data for generating dose distribution graphs and histograms are stored in a memory of the computer system running optimization module 100 for user review and display and the optimized beamlet weights and MLC leaf positions and sequences are output to the radiation delivery system to begin radiation therapy treatment of the patient.

Figure 8:
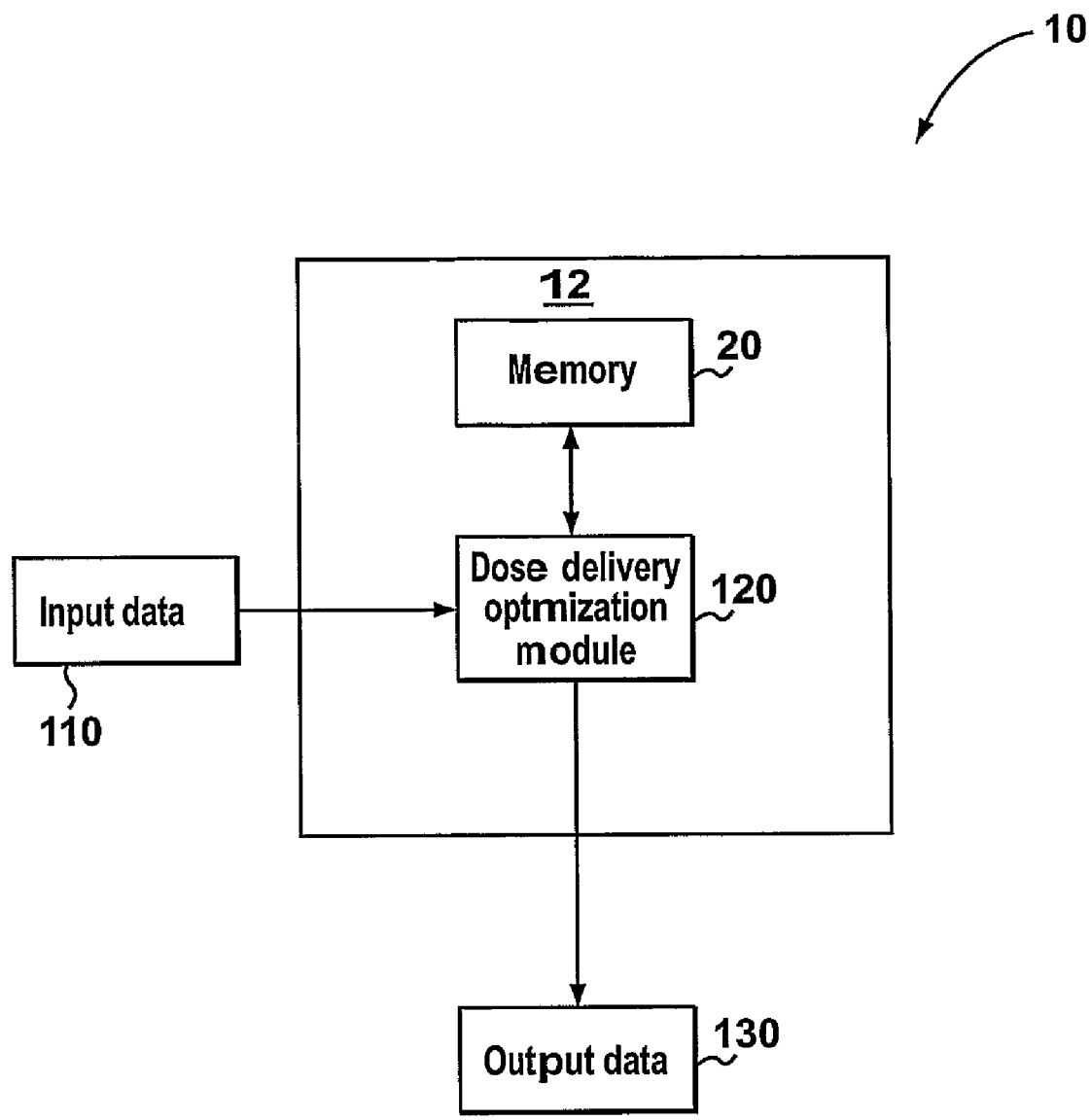
FIG. 8 is a block diagram of a system for dose delivery optimization according to an embodiment of the invention.

While the methods and subprocesses for optimization have been described above in relation to one preferred embodiment, the invention may be embodied also in an optimization system 10, running optimization module 120, as is shown in FIG. 8.

In FIG. 8, optimization system 10 includes a computer system 12 having memory 20 and optimization module 120 running as executable computer program instructions thereon. Memory 20 is fast memory, such as fast-access RAM, for storing arrays and matrices and calculation terms used during the optimization process 100. Memory 20 is also used to store statistics and/or calculations for generating dose-volume histograms and colour-coded dose distribution graphics. Memory 20 may include, or communicate with, secondary (slower) memory to facilitate appropriate data storage during process 100. Optimization module 120 uses memory 20 as required for its storage requirements.

Computer system 12 further includes normal computer peripherals, including graphics displays, keyboard, secondary memory and serial interface, as would normally be used for a computer system which receives input data 110 and generates corresponding output data 130.

In a further aspect, the invention may be embodied in computer program instructions (i.e. software for executing the described methods) stored on computer-readable storage media, such as a hard disk, CD-ROM or RAM.

While preferred embodiments of the invention have been described in relation to dose delivery of radiation for radiation therapy treatment, it is to be understood that the optimization process 100 and optimization system 10 may be equally useful for planning optimized radiation delivery to body volumes other than those of human patients under treatment for cancerous tumors. For example, the described systems and methods may be employed for animals other than humans and may be employed for irradiating non-living tissue or material or organic matter where selective dose delivery of radiation is desired.

Figure 9A:
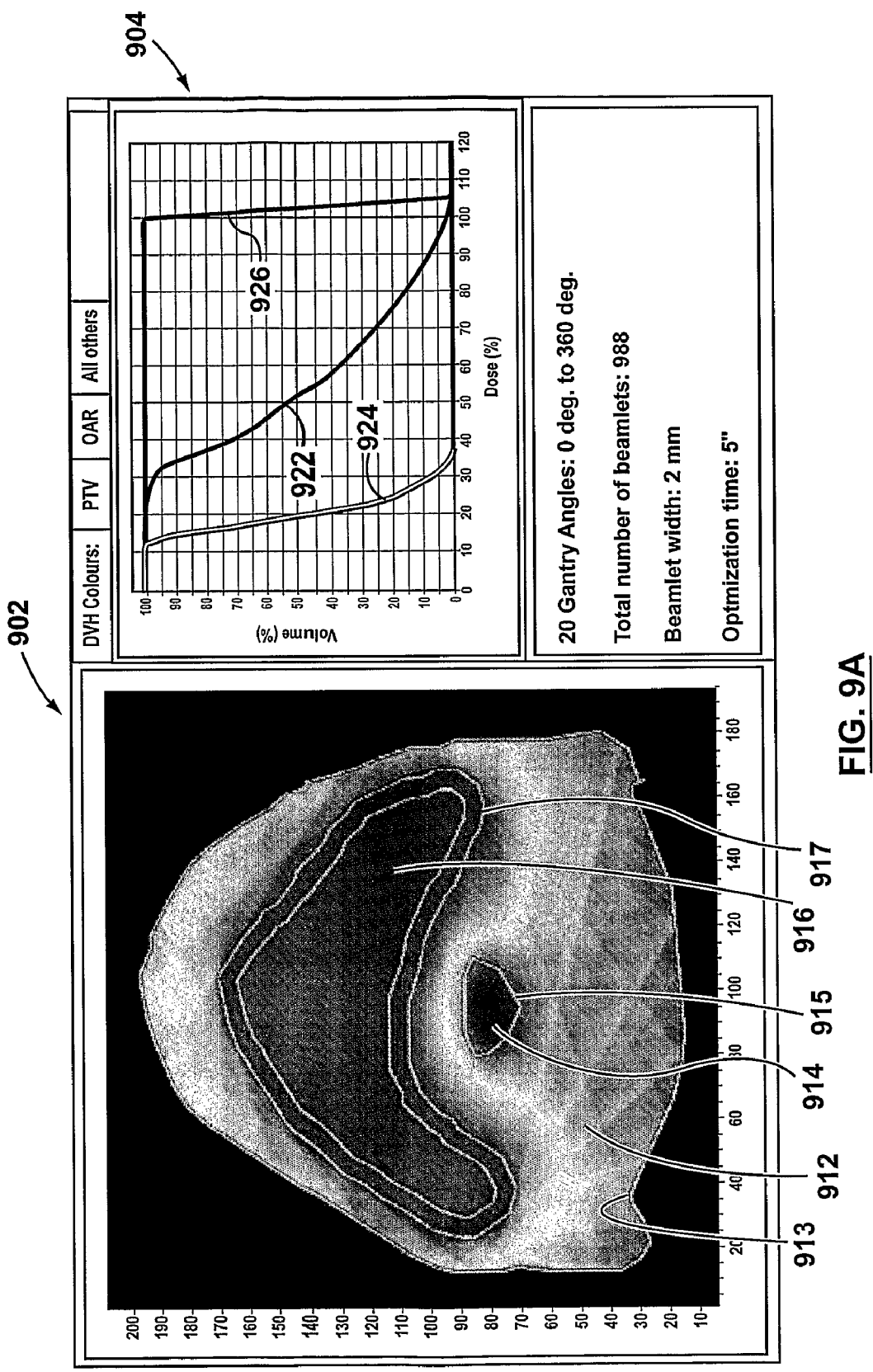
FIGS. 9A to 9D show example optimized dose distribution maps and corresponding dose-volume histograms.
Figure 9B:
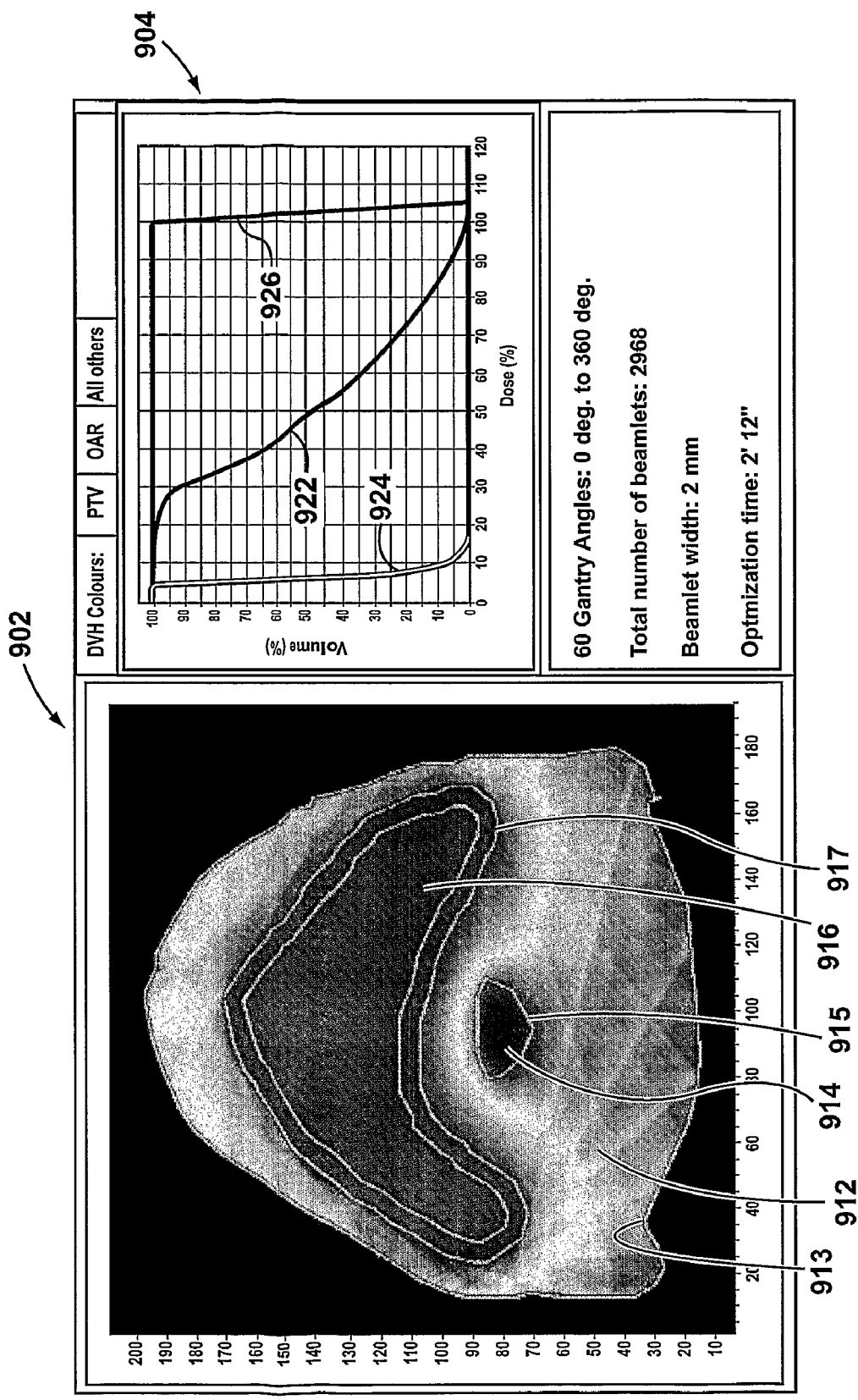

FIGS. 9A to 9D show example optimized dose distribution maps 902 and dose-volume histograms 904 for IMRT. FIGS. 9A and 9B show a dose distribution map 902 of a CT scan slice of a neck tumor. Dose distribution map 902 shows an outer body contour 913 enclosing all volumes of interest. OAR contour 915 encloses an OAR volume 914, which in this example is the spine. PTV contour 917 encloses a PTV volume 916, which is the neck tumor. The remaining volume within outer body contour 913, which is not within OAR and PTV volumes 914 and 916, is called the ATR volume 912.

As the example in FIG. 9A illustrates, it can be difficult to direct beams so as to deliver radiation to the PTV volume 916 without also directing some radiation towards the OAR volume 914. In this example, it is particularly important to minimize delivery of radiation to the spine as it is sensitive to radiation delivery and an excessive dose may result in damage to the spinal cord or nerve endings therein. Typically, dose-volume constraints for an OAR such as the spinal cord are such that none of the OAR volume should receive a dose in excess of about 45 Gy. If only a low number of gantry angles are employed in the optimization planning, this dose-volume constraint may not be able to be met, whereas if a larger number of gantry angles are employed, such a dose-volume constraint can be met. The greater computational efficiency achievable by the invention enables a larger number of gantry angles to be employed, which results in a better conformal mapping of the dose delivery plan.

FIGS. 9A and 9B show the same ATR, OAR and PTV volumes and contours but, whereas FIG. 9A shows the output plan of an optimization using twenty gantry angles, FIG. 9B shows a plan using sixty gantry angles. In FIG. 9B, the OAR curve 924 of dose-volume histogram 904 shows that none of the OAR volume 914 receives more than 20% of the dose, as compared to the 40% indicated in FIG. 9A. The increase in the number of gantry angles allows for greater flexibility in optimizing the dose delivery plan so as to avoid irradiating the OAR while maximizing the radiation dose to the PTV. This increase in the number of gantry angles is enabled by the increased computational efficiency of the present optimization method.

In dose-volume histogram 904, ATR curve 922 indicates the dose-volume distribution of ATR volume 912, while PTV curve 926 indicates the dose-volume distribution to PTV volume 916.

While the optimization is faster for fewer gantry angles (and thus fewer beamlets), for example in the order of 5 seconds, it is less optimized than the plan using sixty gantry angles in the sense that it delivers a higher average dose to the OAR volume 914. Conversely, while the optimization using sixty gantry angles is more accurate in avoiding the OAR volume 914, the time required for the optimization is greater, for example in the order of 2 minutes and 12 seconds.

Figure 9C:
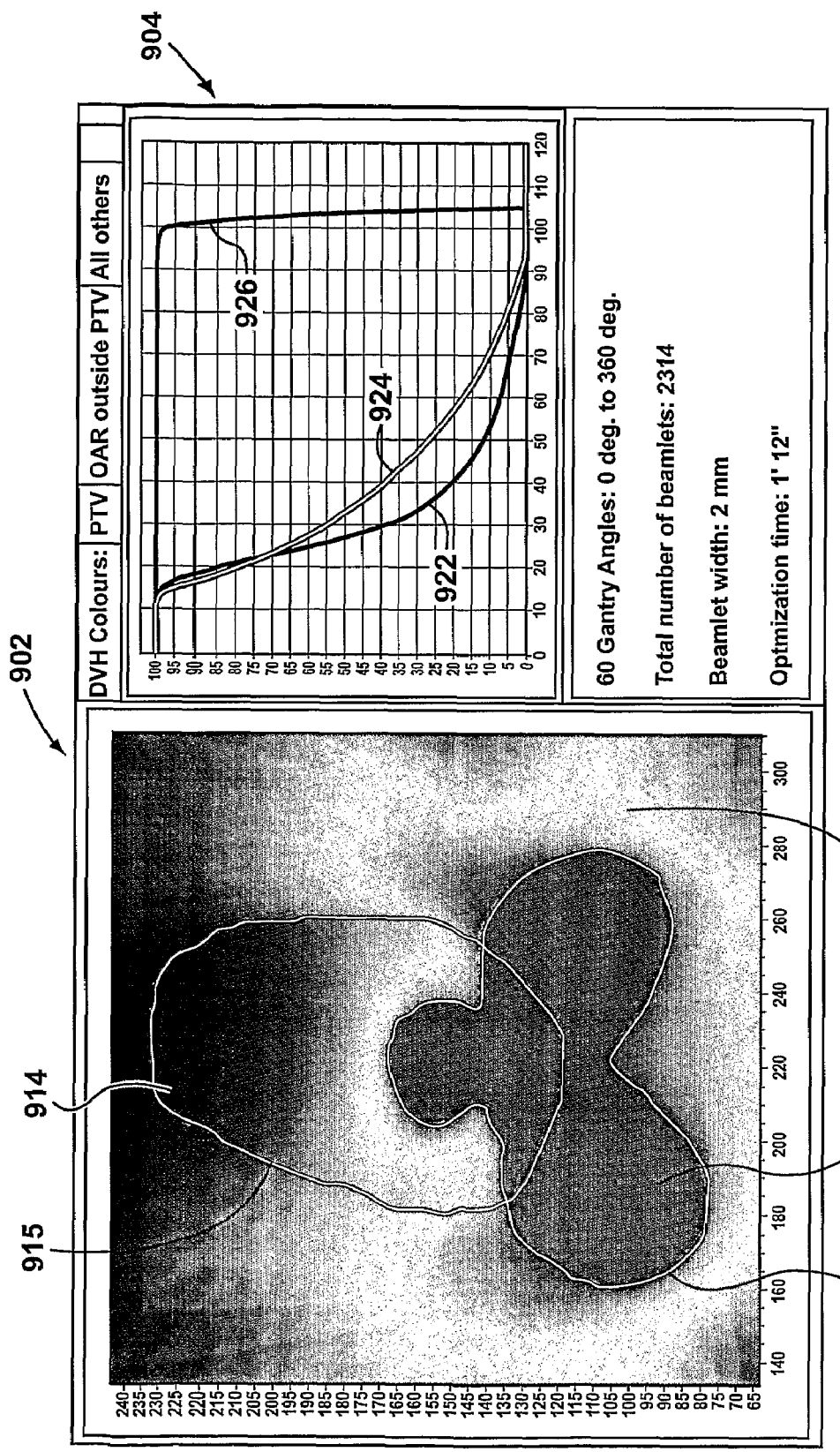
Figure 9D:
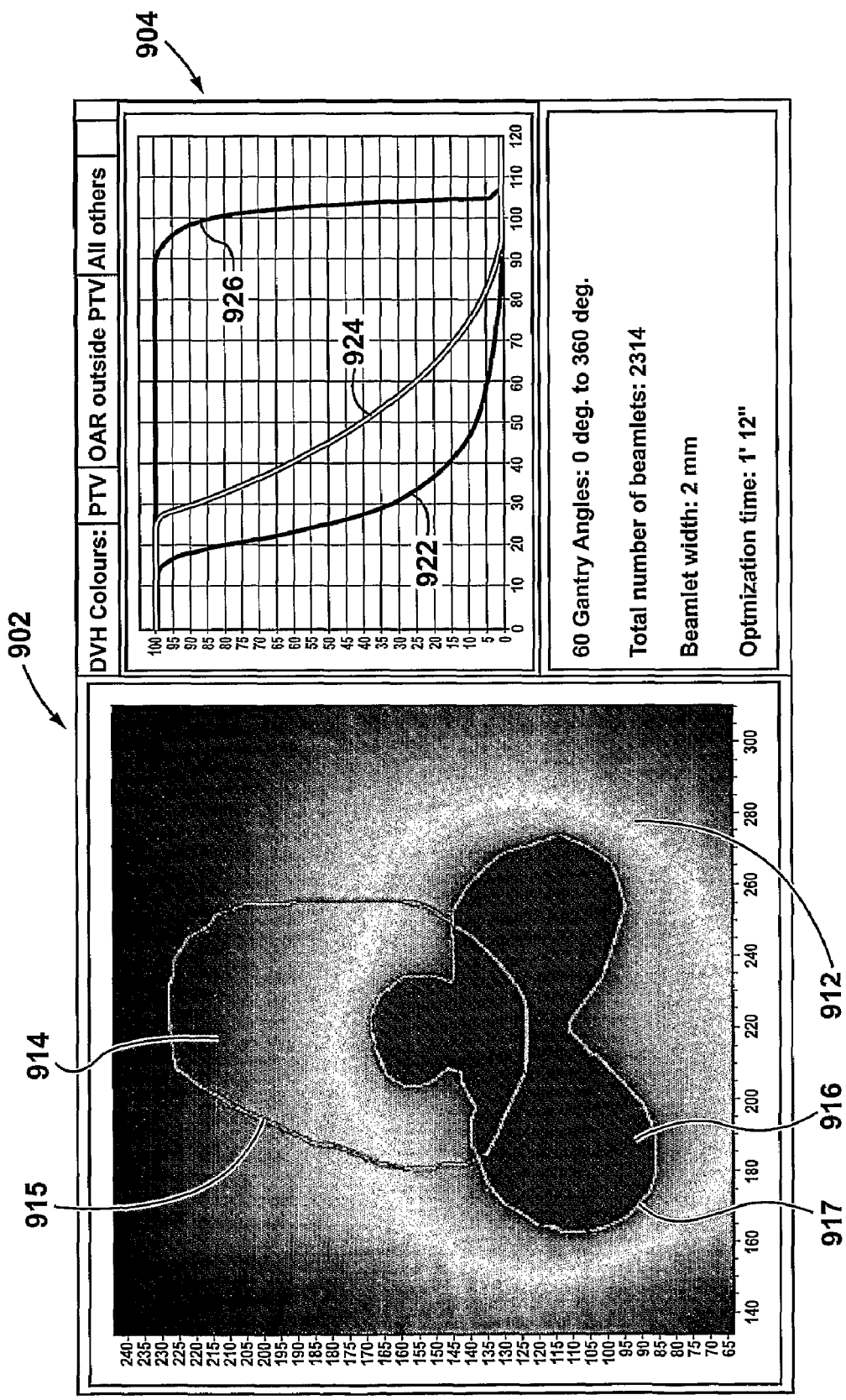

The reference indicators mentioned above in relation to FIGS. 9A and 9B are also applicable to FIGS. 9C and 9D.

FIGS. 9C and 9D show further examples of dose distribution maps 902 and corresponding dose-volume histograms 904. Outer body contour 913 is not shown in FIGS. 9C and 9D because in this example dose distribution map 902 is a close-up within a larger body volume. FIGS. 9C and 9D relate to a planned dose delivery to a prostate tumor, indicated by PTV volume 916. In this example, the OAR volume 914 is the bladder. As can be seen from FIGS. 9C and 9D, the OAR body contour 915 overlaps the PTV contour 917 and therefore it is not possible to minimize dose delivery to the OAR to the same degree as would be possible where the contours and volumes did not overlap.

The optimizations shown in FIGS. 9C and 9D use the same number of IMRT gantry angles and beamlets, with the same beamlet width of 2 mm. The primary difference between FIGS. 9C and 9D is that the optimization shown in FIG. 9D was designed to provide a highly conformal dose distribution to the PTV, with less importance being given to irradiating the OAR. A comparison of OAR curves 924 in FIGS. 9C and 9D indicates that the OAR volume 914 in FIG. 9D received a higher average dose than that of FIG. 9C, primarily because of the lower importance attributed to minimizing irradiation of the OAR in the optimization shown in FIG. 9D. Thus, manipulation of importance coefficients can have a significant effect on the resultant dose distribution within the PTV and OAR.

In this description, certain terms have been used interchangeably. For example, beamlet weights and beamlet intensities have been used interchangeably and are intended to have the same meaning. Similarly, importance parameters and importance coefficients have been used interchangeably and are intended to have the same meaning. Also, some terms used in this description may be called by other names in related technical papers, although the meaning is the same. For example, the term objective function used herein may be called a cost function by others. Similarly, the term fluence is used elsewhere for describing beamlet weights or intensities. It is intended that this description should cover all terms having the same meaning, as would be understood by the skilled person, as the terms used herein. Further reference can be made to the Glossary below.

Glossary

Beam: a ray of radiation transmitted in two or three dimensions.

Beamlet: A fraction of a beam of radiation. A beam can be divided into many small beamlets. For example, a beam with a 10×10 $cm^2$ cross-section can be divided into 100 beamlets with 1×1 $cm^2$ cross-section.

Beamlet Dose Deposit Array: an array of the planned dose deposits by a particular unit weight beamlet in the cells within a particular contour, multiplied by the prescribed dose for that contour.

Beamlet Intersection Matrix: a matrix of the products of the separate planned dose deposits in a cell by intersecting beamlets added over all cells within a particular contour. The diagonal elements of this matrix contain the sum of the squares of the dose deposits of each beamlet over all the cells of the contour.

Beamlet weight: Intensity level of a beamlet.

Contour: a two-dimensional outline of a structure in a single CT scan, outlining, for example, a target volume or an organ or any other internal mass.

Importance Parameter (or coefficient): a relative importance factor used in the optimization process. An importance parameter can be defined in the range from 0 (ie. where the corresponding organ is considered to be irrelevant to the optimization) to any positive value. The higher the value of the importance parameter relative to other importance parameters, the greater the importance attributed to the corresponding term of the objective function and the greater influence that term will have on the optimization of the objective function.

Intensity: a measure of relative strength of radiation.

Non-target volume: the volume outside the target volume but within the body volume. The non-target volume should receive as small a radiation dose as possible.

Objective function: a mathematical function used for optimizing the way radiation is delivered to a body volume.

Organ-at-risk: an organ inside a patient that may be adversely affected or damaged by radiation during radiation therapy. Generally, important organs near a tumor are organs at risk since they may receive high radiation doses. Typical organs at risk are: the spinal cord, eyes, liver, lung, kidney, heart, rectum, bladder, brain stem, optic nerves, optical chiasma, parotid and small intestine.

Planned radiation dose deposit: the calculated radiation dose to be delivered at a point in a patient for a particular plan.

Radiation: Energy radiated or transmitted as rays, waves, in the form of particles. For this application, we refer to high energy x-rays particularly.

Target volume: a contoured volume, for example, including a tumor and surrounding tissue, to receive a certain prescription of radiation dose to treat a tumor or other mass within that volume.

The invention claimed is:

1. A method of dose delivery of radiation comprising the steps of:

determining an objective function to be used for mapping radiation beams to a body volume comprising at least one target volume, and at least one non-target volume, the objective function comprising a first term related to the at least one target volume and a second term related to the at least one non-target volume;

determining an optimal set of weights of beamlets using the objective function, wherein the second term is zero only when the weights of beamlets mapped so as to pass through the at least one non-target volume are zero; and delivering radiation based on the determined optimal set of weights of beamlets.

2. The method of claim 1, wherein the second term comprises, for all of a plurality of non-target volume portions, a non-target volume sum of beamlet sums related to respective non-target volume portions, wherein the beamlet sums are of the form:

$$\sum_{i}^{all-beamlets} w_i^2 d_1^2(x)$$

where $w_i^2$ is the squared weight of beamlet i of a plurality of radiation beams and $d_i^2(x)$ is the squared planned radiation dose deposit by the beamlet i at the respective non-target volume portion.

3. The method of claim 1, wherein the objective function further comprises a third term related to an organ-at-risk (OAR) volume and wherein the third term comprises, for all of a plurality of OAR volume portions, an OAR sum of beamlet sums related to respective OAR volume portions, wherein the beamlet sums are of the form:

$$\sum_{i}^{all-beamlets} w_i^2 d_1^2(x)$$

where $w_i^2$ is the squared weight of beamlet i of a plurality of radiation beams and $d_i^2(x)$ is the squared planned radiation dose deposit by the beamlet i at the respective OAR volume portion.

4. The method of claim 1, wherein the objective function further comprises a symmetry term for enabling symmetrical dose delivery about an axis of the at least one target volume.

5. The method of claim 4, wherein the symmetry term is of the form:

$$O_{SYM} = \sum_{i}^{all-beamlets} (w_i^2 - w_i)$$

where $O_{SYM}$ is the symmetry term, and
  $w_i$ is the weight of beamlet i of a plurality of radiation beams.

6. The method of claim 4, wherein the symmetry term is positive and its minimum is zero when $w_i=1$ for all i, where $w_i$ is the weight of beamlet i of a plurality of radiation beams.

7. The method of claim 1, wherein the step of determining the optimal set of weights of beamlets includes solving a linear system of equations.

8. The method of claim 7, wherein the solution of the linear system of equations is generated using matrix inversion of a beamlet intersection matrix for each beamlet.

9. The method of claim 8, wherein the solution of the linear system of equations is generated by the product of the inverted beamlet intersection matrix with a beamlet dose deposit array.

10. The method of claim 8, wherein the beamlet intersection matrix comprises a sum of organ volume matrices respectively corresponding to the at least one target volume and the at least one non-target volume, each organ volume matrix being weighted by a respective importance parameter.

11. The method of claim 10, wherein the beamlet intersection matrix further comprises a symmetry term having a symmetry importance parameter for weighting the symmetry term.

12. The method of claim 10, wherein the importance parameter weighting each organ volume matrix is determined according to a function of position within the respective organ volume.

13. The method of claim 10, wherein each importance parameter has a predetermined value.

14. The method of claim 7, wherein the linear system of equations is derived from a first derivative of the objective function.

15. The method of claim 1, further comprising:
  receiving contour data relating to a two-dimensional contour of the at least one target volume or the at least one non-target volume;
  determining from the contour data whether the contour is oriented clockwise or anti-clockwise; and
  when the contour is determined to be anti-clockwise, changing the order of the contour data so that the contour is oriented clockwise.

16. The method of claim 15, wherein determining whether the contour is oriented clockwise or anti-clockwise further comprises:
  a) determining a topmost vertex of the contour;
  b) determining a lowermost vertex of the contour;
  c) determining a rightmost vertex of the contour that is neither the topmost or lowermost vertex;
  d) determining a leftmost vertex of the contour that is neither the topmost or lowermost vertex; and
  e) determining the contour orientation according to the relative clockwise order of the topmost, lowermost, rightmost and leftmost vertices with respect to each other.

17. The method of claim 15, further comprising:
  extrapolating a continuous contour from the contour data;
  determining all right and left boundaries of the continuous contour; and
  determining a cell of the body volume to be within the continuous contour when the cell lies between a facing pair of right and left boundaries.

18. The method of claim 17, wherein a boundary is determined to be a left boundary when the contour data indicates an upwardly extending sequence of contour points and a boundary is determined to be a right boundary when the contour data indicates a downwardly extending sequence of contour points.

19. The method of claim 1, wherein said body volume is virtually divided into a plurality of cells of a predetermined size and said radiation beams are mapped to said body volume such that fractions of the radiation beams are dimensioned proportionally to the size of said cells.

20. The method of claim 19, wherein said fractions are resolved into linearly sequential portions of non-uniform size.

21. The method of claim 20, wherein a linear dimension of said sequential portions is uniform and is 1 to 2 times a width dimension of said cells.

22. The method of claim 21, wherein said linear dimension is about 1.25 times said width dimension.

23. The method of claim 1, wherein the dose delivery of radiation comprises intensity-modulated radiation therapy.

24. The method of claim 1, wherein the dose delivery of radiation comprises Tomotherapy.

25. The method of claim 1, wherein each weight of the determined optimal set of weights of beamlets is greater or equal to zero.

26. The method of claim 1, wherein determining the optimal set of weights of beamlets comprises determining a minimum of the objective function.

27. The method of claim 1, wherein determining the optimal set of weights of beamlets comprises determining a maximum of the objective function.

28. A computer-implemented method of determining an objective function to be used for mapping radiation beams to a body volume comprising at least one target volume and at least one non-target volume, the objective function comprising a first term related to the at least one target volume and a second term related to the at least one non-target volume, the method comprising:
   determining an optimal set of weights of beamlets using the objective function, wherein the second term is zero only when the weights of beamlets mapped so as to pass through the at least one non-target volume are zero; and
   making the determined optimal set of weights of beamlets available for use in delivering radiation.

29. The method of claim 28, wherein the second term comprises, for all of a plurality of non-target volume portions, a non-target volume sum of beamlet sums related to respective non-target volume portions, wherein the beamlet sums are of the form:

$$\sum_{i}^{all-beamlets} w_i^2 d_i^2(x)$$

where $w_i^2$ is the squared weight of beamlet i of a plurality of radiation beams and $d_i^2(x)$ is the squared planned radiation dose deposit by the beamlet i at the respective non-target volume portion.

30. The method of claim 28, wherein the objective function further comprises a third term related to an organ-at-risk (OAR) volume and wherein the third term comprises, for all of a plurality of OAR volume portions, an OAR sum of beamlet sums related to respective OAR volume portions, wherein the beamlet sums are of the form:

$$\sum_{i}^{all-beamlets} w_i^2 d_i^2(x)$$

where $w_i^2$ is the squared weight of beamlet i of a plurality of radiation beams and $d_i^2(x)$ is the squared planned radiation dose deposit by the beamlet i at the respective OAR volume portion.

31. The method of claim 28, wherein the objective function further comprises a symmetry term for enabling symmetrical dose delivery about an axis of the at least one target volume.

32. The method of claim 31, wherein the symmetry term is of the form:

$$O_{SYM} = \sum_{i}^{all-beamlets} (w_i^2 - w_i)$$

where $O_{SYM}$ is the symmetry term, and
   $w_i$ is the weight of beamlet i of a plurality of radiation beams.

33. The method of claim 31, wherein the symmetry term is positive and its minimum is zero when $w_i=1$ for all i, where $w_i$ is the weight of beamlet i of a plurality of radiation beams.

34. The method of claim 28, further comprising delivering radiation based on the determined optimal set of weights of beamlets.

35. The method of claim 34, wherein the delivery of radiation comprises intensity-modulated radiation therapy.

36. The method of claim 34, wherein the delivery of radiation comprises Tomotherapy.

37. A method of providing radiation, comprising:
   determining an objective function for optimizing radiation dose delivery to a target volume, the objective function having a symmetry term for enabling symmetrical dose delivery about an axis of the target volume; and
   providing radiation based on the objective function.

38. The method of claim 37, wherein the symmetry term is of the form:

$$O_{SYM} = \sum_{i}^{all-beamlets} (w_i^2 - w_i)$$

where $O_{SYM}$ is the symmetry term, and
   $w_i$ is the weight of beamlet i of a plurality of radiation beams.

39. The method of claim 37, wherein the symmetry term is positive and its minimum is zero when $w_i=1$ for all i, where $w_i$ is the weight of beamlet i of a plurality of radiation beams.

40. The method of claim 37, wherein providing radiation comprises providing intensity-modulated radiation therapy.

41. The method of claim 37, wherein providing radiation comprises providing Tomotherapy.

42. A system for optimizing dose delivery of radiation comprising:
   computer processing means for determining an objective function to be used for mapping radiation beams to a body volume comprising at least one target volume, and at least one non-target volume, the objective function comprising a first term related to the at least one target volume and a second term related to the at least one non-target volume, the computer processing means being arranged to determine an optimal set of weights of beamlets using the objective function, wherein the second term is zero only when the weights of beamlets mapped so as to pass through the at least one non-target volume are zero; and
   data communication means operably associated with the computer processing means for providing data to a radiation delivery apparatus for delivering radiation to the body volume based on the determined optimal set of weights of beamlets.

43. The system of claim 42, wherein the dose delivery of radiation comprises intensity-modulated radiation therapy.

44. The system of claim 42, wherein the dose delivery of radiation comprises Tomotherapy.

45. Computer readable storage having stored thereon computer program instructions executable on a computer system for causing the computer system to perform a method comprising:
   determining an objective function to be used for mapping radiation beams for a body volume comprising at least one target volume and at least one non-target volume, the objective function comprising a first term related to the at least one target volume and a second term related to the at least one non-target volume;

determining an optimal set of weights of beamlets using the objective function, wherein the second term is zero only when the weights of beamlets mapped so as to pass through the at least one non-target volume are zero; and making the determined optimal set of weights of beamlets available for use in delivering radiation.

\* \* \* \* \*